US011071483B2

(12) United States Patent
Egi et al.

(10) Patent No.: US 11,071,483 B2
(45) Date of Patent: Jul. 27, 2021

(54) MOOD SCORE CALCULATION APPARATUS AND MOOD SCORE CALCULATION METHOD

(71) Applicant: HITACHI, LTD., Tokyo (JP)

(72) Inventors: Masashi Egi, Tokyo (JP); Masashi Kiguchi, Tokyo (JP); Hirokazu Atsumori, Tokyo (JP)

(73) Assignee: HITACHI, LTD., Tokyo (JP)

( * ) Notice: Subject to any disclaimer, the term of this patent is extended or adjusted under 35 U.S.C. 154(b) by 271 days.

(21) Appl. No.: 15/934,452

(22) Filed: Mar. 23, 2018

(65) Prior Publication Data

US 2019/0110727 A1 Apr. 18, 2019

(30) Foreign Application Priority Data

Oct. 17, 2017 (JP) ............................ JP2017-200767

(51) Int. Cl.

| | |
|---|---|
| ***A61B 5/16*** | (2006.01) |
| ***G16H 10/60*** | (2018.01) |
| ***G06F 16/28*** | (2019.01) |
| ***G06F 16/335*** | (2019.01) |
| ***G16H 50/70*** | (2018.01) |
| ***G16H 50/30*** | (2018.01) |
| ***G16H 20/70*** | (2018.01) |

(52) U.S. Cl.

CPC ............ *A61B 5/165* (2013.01); *G06F 16/285* (2019.01); *G06F 16/337* (2019.01); *G16H 10/60* (2018.01); *G16H 50/30* (2018.01); *G16H 50/70* (2018.01); *G16H 20/70* (2018.01)

(58) Field of Classification Search

CPC ..... A61B 5/165; G06F 16/337; G06F 16/285; G16H 50/70; G16H 50/30; G16H 10/60; G16H 20/70

See application file for complete search history.

(56) References Cited

U.S. PATENT DOCUMENTS

| | | | | |
|---|---|---|---|---|
| 9,721,066 | B1 * | 8/2017 | Funaro | G16H 50/30 |
| 9,928,462 | B2 | 3/2018 | Lee | |
| 2013/0080127 | A1 * | 3/2013 | Shahaf | G06F 19/00 703/2 |

(Continued)

FOREIGN PATENT DOCUMENTS

| | | | |
|---|---|---|---|
| JP | 2010-131280 | A | 6/2010 |
| JP | 05319960 | B2 | 7/2013 |

(Continued)

OTHER PUBLICATIONS

Japanese Office Action dated Apr. 20, 2021 for Japanese Patent Application No. 2017-200767.

*Primary Examiner* — Pierre M Vital
*Assistant Examiner* — Zuheir A Mheir
(74) *Attorney, Agent, or Firm* — Volpe Koenig

(57) ABSTRACT

A mood score calculation apparatus has a memory device that stores a manipulation history of a user on a predetermined device and a arithmetic device that classifies the manipulation history into any one of a verbal task and a spatial task on the basis of a predetermined algorithm, calculates the user's mood score on the basis of a relative relationship between the manipulation histories for each of the verbal task and the spatial task specified in the classification, and outputs information on the mood score into a predetermined output target.

4 Claims, 21 Drawing Sheets

(56) References Cited

U.S. PATENT DOCUMENTS

| | | | | |
|---|---|---|---|---|
| 2013/0253329 | A1* | 9/2013 | Sato | A61B 5/165<br>600/473 |
| 2015/0256675 | A1* | 9/2015 | Sri | H04L 12/1827<br>379/265.09 |
| 2017/0337834 | A1* | 11/2017 | Shindi | A61B 5/0482 |
| 2018/0181854 | A1* | 6/2018 | Koukoumidis | G06N 3/006 |
| 2018/0191837 | A1* | 7/2018 | Christophe | H04L 67/306 |
| 2018/0353108 | A1* | 12/2018 | Prate | H04L 67/22 |

FOREIGN PATENT DOCUMENTS

| | | | |
|---|---|---|---|
| JP | 2014-094291 | A | 5/2014 |
| WO | 2016/203575 | A1 | 12/2016 |

* cited by examiner

MANIPULATION INFORMATION 140

| EMPLOYEE TERMINAL ID (141) | DATE (142) | TIME (143) | EVENT NAME (144) | KEY TYPE (145) | APPLICATION NAME (146) |
|---|---|---|---|---|---|
| PC0001 | 2014/03/13 | 10:21:01.997 | KEY_DOWN | CHAR | TABLE CALCULATION |
| PC0001 | 2014/03/13 | 10:21:01.212 | KEY_UP | CHAR | TABLE CALCULATION |
| PC0001 | 2014/03/13 | 10:21:09.061 | KEY_DOWN | RETURN | TABLE CALCULATION |
| PC0001 | 2014/03/13 | 10:21:09.294 | KEY_UP | RETURN | TABLE CALCULATION |
| PC0001 | 2014/03/13 | 10:21:13.815 | L_BUTTON_DOWN | – | DRAWING |
| PC0001 | 2014/03/13 | 10:21:14.003 | L_BUTTON_UP | – | DRAWING |
| ... | ... | ... | ... | ... | ... |

FIG. 4

MANIPULATION TIME-SERIES TABLE 105

| EMPLOYEE TERMINAL ID (151) | DATE (152) | TIME (153) | EVENT NAME (154) | KEY TYPE (155) | APPLICATION NAME (156) |
|---|---|---|---|---|---|
| PC0001 | 2014/03/13 | 10:21:01.997 | KEY_DOWN | CHAR | TABLE CALCULATION |
| PC0001 | 2014/03/13 | 10:21:01.212 | KEY_UP | CHAR | TABLE CALCULATION |
| PC0001 | 2014/03/13 | 10:21:09.061 | KEY_DOWN | RETURN | TABLE CALCULATION |
| PC0001 | 2014/03/13 | 10:21:09.294 | KEY_UP | RETURN | TABLE CALCULATION |
| PC0001 | 2014/03/13 | 10:21:13.815 | L_BUTTON_DOWN | – | DRAWING |
| PC0001 | 2014/03/13 | 10:21:14.003 | L_BUTTON_UP | – | DRAWING |
| ... | ... | ... | ... | ... | ... |
| PC0002 | 2014/03/13 | 10:21:13.122 | KEY_DOWN | DOWN | DOCUMENT CREATION |
| PC0002 | 2014/03/13 | 10:21:13.361 | KEY_UP | DOWN | DOCUMENT CREATION |
| PC0002 | 2014/03/13 | 10:21:14.001 | KEY_DOWN | DELETE | DOCUMENT CREATION |
| PC0002 | 2014/03/13 | 10:21:14.202 | KEY_UP | DELETE | DOCUMENT CREATION |
| PC0002 | 2014/03/13 | 10:21:14.597 | L_BUTTON_DOWN | RIGHT | DOCUMENT CREATION |
| PC0002 | 2014/03/13 | 10:21:14.808 | L_BUTTON_UP | RIGHT | DOCUMENT CREATION |
| ... | ... | ... | ... | ... | ... |

| # | TIME |
|---|---|
| 1 | 10:21:01.997 |
| 2 | 10:21:09.061 |
| ... | ... |

TIME VARIATION TABLE 160

| EMPLOYEE TERMINAL ID | DATE | VERBAL TASK | | | SPATIAL TASK | | |
|---|---|---|---|---|---|---|---|
| | | TOTAL NUMBER OF TARGET EVENTS | VARIATION FEATURE AMOUNT | DETERMINANT | TOTAL NUMBER OF TARGET EVENTS | VARIATION FEATURE AMOUNT | DETERMINANT |
| PC0001 | 2014/03/13 | 1273 | 0.712 | 0.9998 | 314 | 0.887 | 0.9900 |
| PC0001 | 2014/03/14 | 991 | 0.709 | 0.9985 | 159 | 0.690 | 0.9952 |
| PC0001 | 2014/03/17 | 2720 | 0.609 | 0.8920 | 265 | 0.752 | 0.9883 |
| ··· | ··· | ··· | ··· | ··· | ··· | ··· | ··· |
| PC0002 | 2014/03/13 | 3455 | 0.698 | 0.9929 | 189 | 0.701 | 0.9779 |
| PC0002 | 2014/03/14 | 13 | NaN | NaN | 232 | 0.764 | NaN |
| PC0002 | 2014/03/17 | 1064 | 0.788 | 0.9999 | 138 | 0.655 | 0.9945 |
| ··· | ··· | ··· | ··· | ··· | ··· | ··· | ··· |

FEATURE AMOUNT ANALYSIS RESULT TABLE 180

| EMPLOYEE TERMINAL ID | DATE | MOOD SCORE |
|---|---|---|
| PC0001 | 2014/03/13 | 9.12 |
| PC0001 | 2014/03/14 | 9.09 |
| PC0001 | 2014/03/17 | ABNORMAL |
| ・・・ | ・・・ | ・・・ |
| PC0002 | 2014/03/13 | 8.98 |
| PC0002 | 2014/03/14 | NaN |
| PC0002 | 2014/03/17 | 9.88 |
| ・・・ | ・・・ | ・・・ |

MOOD SCORE ANALYSIS RESULT TABLE 190

FIG. 13

MOOD SCORE CALCULATION APPARATUS AND MOOD SCORE CALCULATION METHOD

CROSS-REFERENCE TO RELATED APPLICATION

This application claims priority pursuant to 35 U.S.C. § 119 from Japanese Patent Application No. 2017-200767, filed on Oct. 17, 2017, the entire disclosure of which is incorporated herein by reference.

BACKGROUND

The present invention relates to a mood score calculation apparatus and a mood score calculation method. Specifically, the present invention relates to a technology for easily and accurately specifying a worker's mental health state in a form less burdensome for the worker.

A social loss caused by mental health disorders is estimated to 2 trillion yen per year in Japan, which becomes a big social problem. Especially, there are many workers suffering from diseases in workplaces, and it is an important issue to find a preventive and premature diagnostic method and help works who were absent due to a mental health disorder to efficiently return to the workplace.

Under such circumstances, a scientific quantification technique for mental health states of workers is required. In general, as a measure to quantify the states of workers in mental health management, the working hour of workers or the mood at work is assessed.

Assessment of the working hours can be relatively easily performed by recording an ON/OFF time of a personal computer (PC) power supply, or the like.

Meanwhile, mood assessment has been performed on the basis of a profile of mood state (POMS) technique, a Beck depression inventory second edition (BDI-II), or the like.

However, when performing the mood assessment described above, an examinee is required to answer dozens of questions in every test, which is a heavy burden. For this reason, it is difficult to perform the assessment on a daily basis. In this regard, there is a demand for a method for quantitatively assessing the daily mood without imposing burdens on examinees.

As a technique of the prior art based on such a background, there is disclosed a mood score calculation apparatus including a processor and a memory, the memory storing relationship information representing a relationship between a mood score of a user and a feature amount representing variation of a manipulation time interval of a user's terminal, and the processor acquiring a manipulation history of a first user's terminal, calculating a value of the feature amount representing variation of the manipulation time interval of the first user's terminal from the manipulation history, determining a mood score of the user of the first user's terminal on the basis of the value of the feature amount and the relationship information, and outputting the mood score (for example, see WO2016/203575).

In addition, there is disclosed a living body optical measurement apparatus including: a light source that irradiates light onto a test target object; a detector that detects light propagating through the test target object from the light source; a stimulus presenting unit that presents, to the test target object, a first task using language information and a second task using positions of a plurality of pieces of information presented by the presenting unit; and a computation unit that calculates a hemoglobin signal depending on a change of concentrations of oxygenation hemoglobins and deoxygenation hemoglobins inside the test target object from the light detected by the detector, wherein the computation unit calculates each of the hemoglobin signals corresponding to each of the first and second tasks, calculates a relative value or ratio between the hemoglobin signal corresponding to the first task and the hemoglobin signal corresponding to the second task, and assesses a mood of the test target object on the basis of the relative value or the ratio (for example, see Japanese Patent No. 5319960).

However, the techniques of the related art fail to consider a difference of the load on the working memory in the examinee's brain caused by a difference in work content or the employed tool of the terminal or the like by the examinee.

In other words, the mood score obtained by processing the manipulation history of the terminal or the like only from the statistical viewpoint does not reflect the neuroscientific knowledge, and it is difficult to expect excellent accuracy.

Meanwhile, if an examinee wears a near-infrared brain measurement device and is subjected to a series of tasks, the examinee is released from the stress of answering every question one by one. However, attaching such a measurement device itself is another stress, and the burden on the examinee occurs in another form.

When a lot of examinees take examination at the same time, it is necessary to prepare the measurement devices as many as the number of examinees, and the cost or effort for introducing and operating the measurement devices becomes not negligible. In addition, it is necessary to assign a certain period of time to the aforementioned tasks on a daily basis for such a lot of examinees, that is, workers. This is not realistic in consideration of the original tasks of the workers.

SUMMARY

In view of the aforementioned problems, it is therefore an object of the invention to provide a technology for easily and accurately specifying a worker's mental health state in a form less burdensome for the worker.

According to an aspect of the invention, there is provided a mood score calculation apparatus including: a memory device that stores a manipulation history of a user on a predetermined device; and a arithmetic device that classifies the manipulation history into any one of a verbal task and a spatial task on the basis of a predetermined algorithm, calculates a mood score of the user on the basis of a relative relationship between manipulation histories for each of the verbal task and the spatial task specified in the classification, and outputs information on the mood score to a predetermined output target.

According to another aspect of the invention, there is provided a mood score calculation method causing an information processing device having a memory device that stores a manipulation history of a user on a predetermined device to perform: classifying the manipulation history into any one of a verbal task and a spatial task on the basis of a predetermined algorithm; calculating a mood score of the user on the basis of a relative relationship between the manipulation histories for each of the verbal task and the spatial task specified in the classification; and outputting information on the mood score to a predetermined output target.

According to the present invention, it is possible to easily and accurately specify a worker's mental health state in a form less burdensome for the worker.

BRIEF DESCRIPTION OF THE DRAWINGS

FIG. 4 is a diagram illustrating an exemplary configuration of manipulation information according to an embodiment of the invention;

FIG. 6 is a diagram illustrating an exemplary configuration of a manipulation time-series table according to an embodiment of the invention;

FIG. 8 is a diagram illustrating an exemplary configuration of a time variation table according to an embodiment of the invention;

FIG. 11 is a diagram illustrating an exemplary configuration of a feature amount analysis result table according to an embodiment of the invention;

FIG. 13 is a diagram illustrating an exemplary configuration of a mood score analysis result table according to an embodiment of the invention;

DETAILED DESCRIPTION OF EMBODIMENTS

<Network Configuration>

Figure 1:
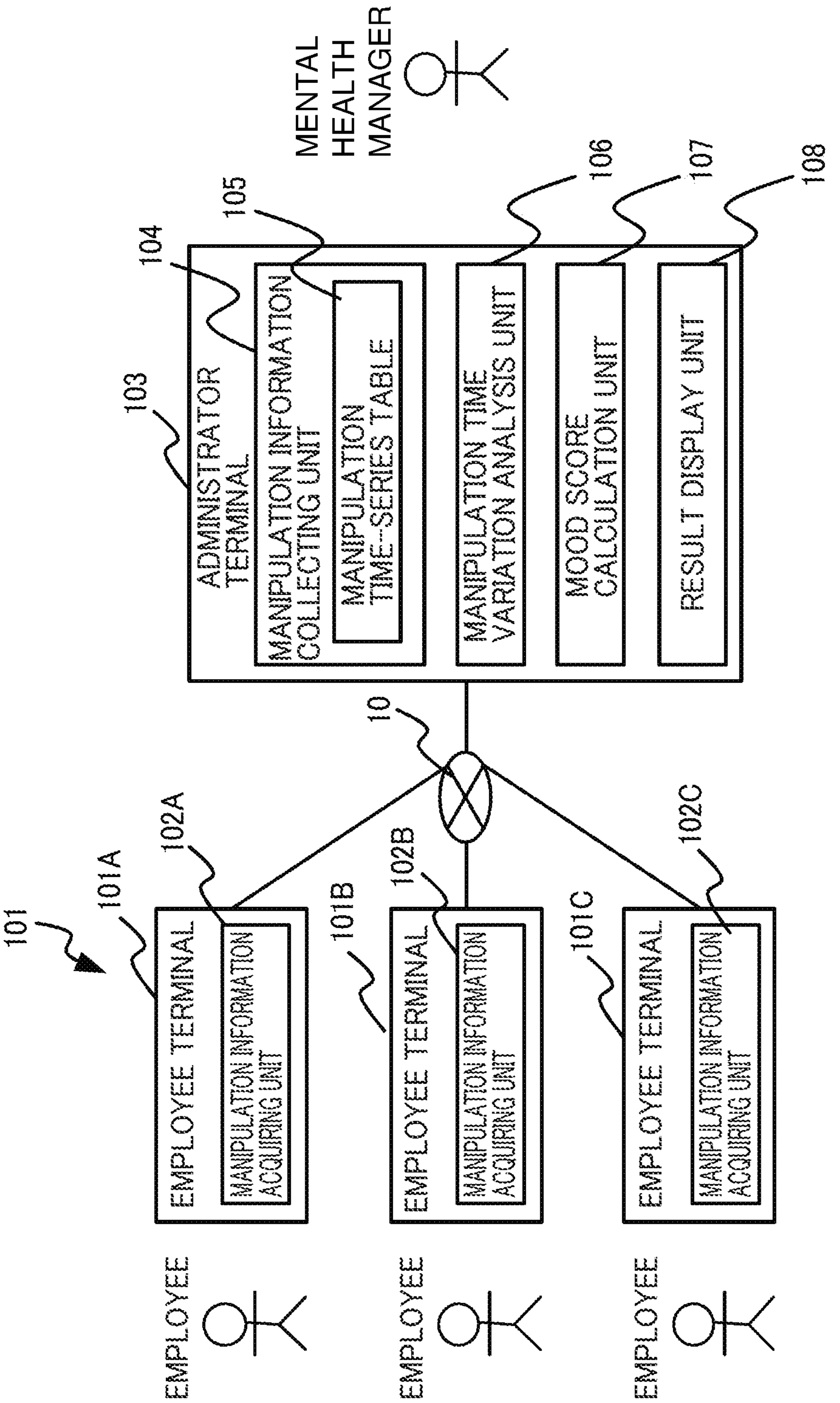
FIG. 1 is a diagram illustrating an exemplary network layout including a mood score calculation apparatus according to an embodiment of the invention.

Embodiments of the invention will now be described in details with reference to the accompanying drawings. FIG. 1 is a network layout diagram including an administrator terminal 103 serving as a mood score calculation apparatus according to an embodiment of the invention. The administrator terminal 103 as the mood score calculation apparatus illustrated in FIG. 1 (hereinafter, referred to as an "administrator terminal 103") is a computing device that easily and accurately specifying a worker's mental health state in a form less burdensome for the worker.

Through the research of the inventors, it was found that a variation of a manipulation time interval on a terminal used by a user was related to the user's mood. In particular, a fractal dimension of the manipulation time interval and a power index of the cumulative probability distribution of the manipulation time interval are highly related to the mood score. It was also found that there is a difference in a load on the working memory of the user's brain depending on which of a verbal task and a spatial task the work content and the employed tool of the terminal are for. It is possible to easily and accurately specify the mood score by reflecting the neuroscientific knowledge without a special burden on the user by reviewing a feature amount representing attributes of the work content or the employed tool, that is, a feature amount representing a variation of the manipulation time interval of each of the verbal task and the spatial task and calculating the mood score on the basis of a relationship therebetween.

Such an administrator terminal 103 is coupled to a plurality of employee terminals 101A to 101C via a network 10. The employee, that is, the worker is a user of each employee terminal 101A to 101C and carries out works using the employee terminals 101A to 101C. Meanwhile, the administrator terminal 103 is used by a mental health manager. The employee terminals 101A to 101C and the administrator terminal 103 may collectively constitute a mood score calculation system. Note that the employee terminals 101A to 101C will be collectively referred to as an employee terminal 101 unless specified otherwise.

The employee terminals 101A to 101C described above have manipulation information acquiring units 102A to 102C, respectively. The manipulation information acquiring units 102A to 102C store manipulation histories of the employee terminals 101A to 101C, respectively, performed by the employee and transmit the manipulation histories to the administrator terminal 103 via the network 10 at a predetermined timing. For this processing, it is assumed that the manipulation information acquiring units 102A to 102C acquire manipulation information performed on an input device such as a keyboard or a mouse provided in the employee terminal from a log function provided in advance in an operating system (OS) or the like, and store the manipulation information in a secondary memory including a nonvolatile memory device.

Note that, unless specified otherwise, the manipulation information acquiring units 102A to 102C are collectively referred to as a manipulation information acquiring unit 102. According to this embodiment, one employee uses one employee terminal 101. Alternatively, a plurality of employees may use one employee terminal 101. It is assumed a manipulation of each employee is distinguished by an employee ID during log-in operation of the employee terminal 101, and this is also reflected on the manipulation history.

Meanwhile, administrator terminal 103 includes a manipulation information collecting unit 104, a manipulation time variation analysis unit 106, a mood score calculation unit 107, and a result display unit 108.

The manipulation information collecting unit 104 collects manipulation histories of employees from the employee terminals 101A to 101C at a predetermined timing via the network 10 and stores the manipulation histories in a manipulation time-series table 105.

The manipulation time variation analysis unit 106 analyzes the manipulation history of each employee collected by the manipulation information collecting unit 104 described above and determines a variation of the manipulation time interval in each manipulation of a verbal task and a spatial task of each employee.

The mood score calculation unit 107 calculates the mood scores of each employee on the basis of a result of the analysis of the manipulation time variation analysis unit 106 described above.

The result display unit 108 displays a result of measuring the mood of each employee, including information on the mood score obtained from the mood score calculation unit 107 described above, on a display device such as a display.

Note that it is assumed that each functional unit such as the manipulation information collecting unit 104, the manipulation time variation analysis unit 106, the mood score calculation unit 107, and the result display unit 108 described above is implemented by executing corresponding programs (described below) of the administrator terminal 103.

<Hardware Configuration>

Figure 2:
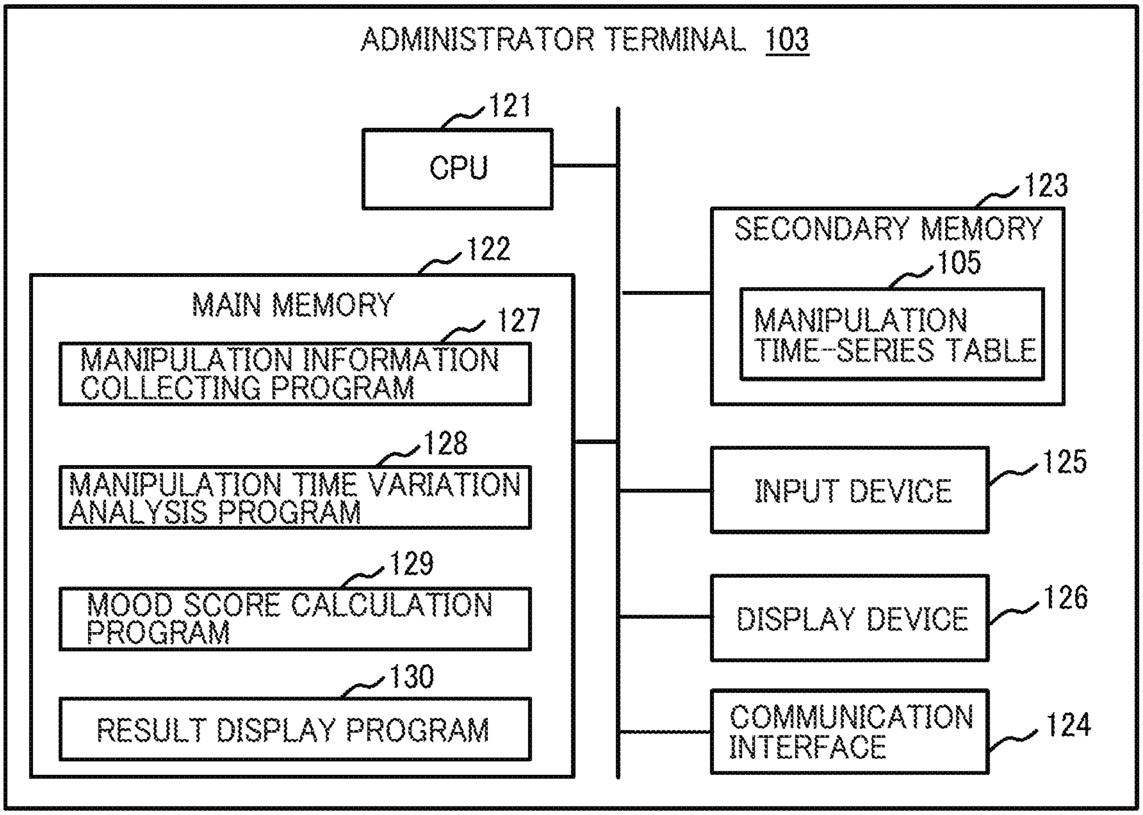
FIG. 2 is a diagram illustrating an exemplary configuration of an administrator terminal according to an embodiment of the invention.

FIG. 2 is a diagram illustrating an exemplary hardware configuration of the administrator terminal 103 according to this embodiment. The administrator terminal 103 according to this embodiment includes, similar to that of a general computer, a central processing unit (CPU) 121 as an arithmetic device, a main memory 122, a secondary memory 123, a communication interface 124 that performs data communication with other devices via the network 10, an input device 125 such as a keyboard or a mouse, and a display device 126 such as a display.

Note that the main memory 122 of the aforementioned configuration is typically a volatile semiconductor memory device. In addition, the secondary memory 123 is typically a nonvolatile memory device including a non-transitory memory medium such as a hard disk drive (HDD) or a solid state drive (SSD).

The main memory 122 stores programs and data used by the programs or the like. In addition, the secondary memory 123 has a nonvolatile non-transitory memory medium for storing programs and data loaded on the main memory 122 described above. Alternatively, the secondary memory 123 may be an external storage device coupled via the network 10.

Each program stored in the main memory 122 may be installed by a program distribution server or a computer readable non-transitory memory medium.

In FIG. 2, the main memory 122 stores an operating system (OS) (not shown) in addition to a manipulation information collecting program 127, a manipulation time variation analysis program 128, a mood score calculation program 129, and a result display program 130 loaded from the secondary memory 123.

The secondary memory 123 stores the manipulation time-series table 105 loaded on the main memory 122.

Note that each program 127 to 130 described above is executed by each processor (CPU 121) and serves as the functional units 104 and 106 to 108 described in conjunction with FIG. 1 to perform predetermined processes. Therefore, according to this disclosure, when a program is described as a subjective, the program may be substituted with a processor. Alternatively, the process executed by the program is a process performed by an apparatus and a system where this program is operated.

The processor may operate as a functional unit that implements a predetermined function by operating on the basis of a program. For example, the CPU 121 operates on the basis of the manipulation information collecting program 127, the manipulation time variation analysis program 128, the mood score calculation program 129, and the result display program 130 to function as the manipulation information collecting unit 104, the manipulation time variation analysis unit 106, the mood score calculation unit 107, and the result display unit 108.

Note that the employee terminals 101A to 101C may have hardware configurations similar to that of the administrator terminal 103. The processors of the employee terminals 101A to 101C execute the manipulation information acquiring program to function as the manipulation information acquiring units 102A to 102C, respectively.

<Mood Score Calculation Sequence and Others>

An actual sequence of the mood score calculation method according to this embodiment will now be described with reference to the accompanying drawings. Various operations of the mood score calculation method described below are implemented by a program read and executed by the administrator terminal 103 on a memory or the like. In addition, this program consists of codes for performing various operations described below.

Figure 3:
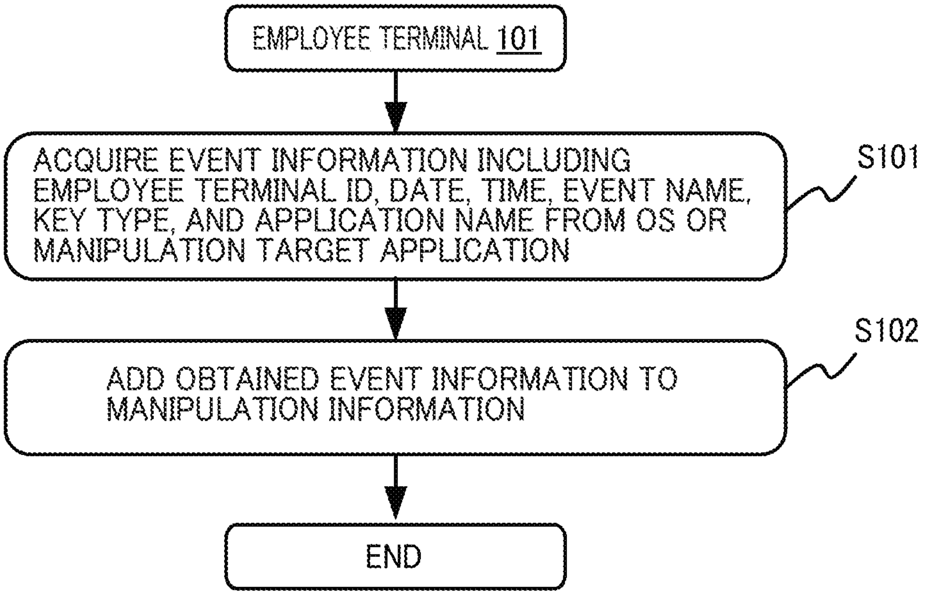
FIG. 3 is a diagram illustrating a first flow example of a mood score calculation method according to an embodiment of the invention.

FIG. 3 is a diagram illustrating a first flow example of the mood score calculation method according to this embodiment. Specifically, FIG. 3 illustrates an operation flow example of the manipulation information acquiring unit 102A of the employee terminal 101A. Note that it is assumed that this flow is executed for every event caused by a manipulation performed by an employee on the employee terminal 101A. This similarly applies to other employee terminals 101B and 101C.

In this case, the manipulation information acquiring unit 102A acquires event information from the OS or the manipulation target application (S101). The event information includes an employee terminal ID of the employee who performs the corresponding manipulation, a manipulation date and time, an event name, a key type manipulated on the input device of the corresponding employee terminal 101A, and the application name.

The manipulation information acquiring unit 102A adds the event information acquired in step S101 to the manipulation information 140 (S102) and terminates the process. This manipulation information 140 is stored, for example, in the secondary memory.

FIG. 4 illustrates an exemplary configuration of manipulation information 140 created by the manipulation information acquiring unit 102A. The input device manipulated by the employee on the employee terminal 101A includes, for example, a keyboard, a mouse, and a touch screen. In addition, the manipulation information 140 includes an employee terminal ID column 141, a date column 142, a time column 143, an event name column 144, a key type column 145, and an application name column 146 as described above.

A single record of such manipulation information 140 represents a single event caused by a manipulation of an employee. A single record corresponds to a single manipulation. Depending on design, a single manipulation may correspond to a single or a plurality of events. For example, each of a keydown event and a keyup event may correspond to a single manipulation, or a set of keydown and keyup events may correspond to a single manipulation.

The employee terminal ID column 141 shows IDs of the manipulated employee terminals. The date column 142 and the time column 143 show dates and times at which the event occurs. The event name column 144 shows names of the occurring events. The key type column 145 shows types of the manipulated keys when the manipulated input device is a keyboard or a touch screen.

Figure 5:
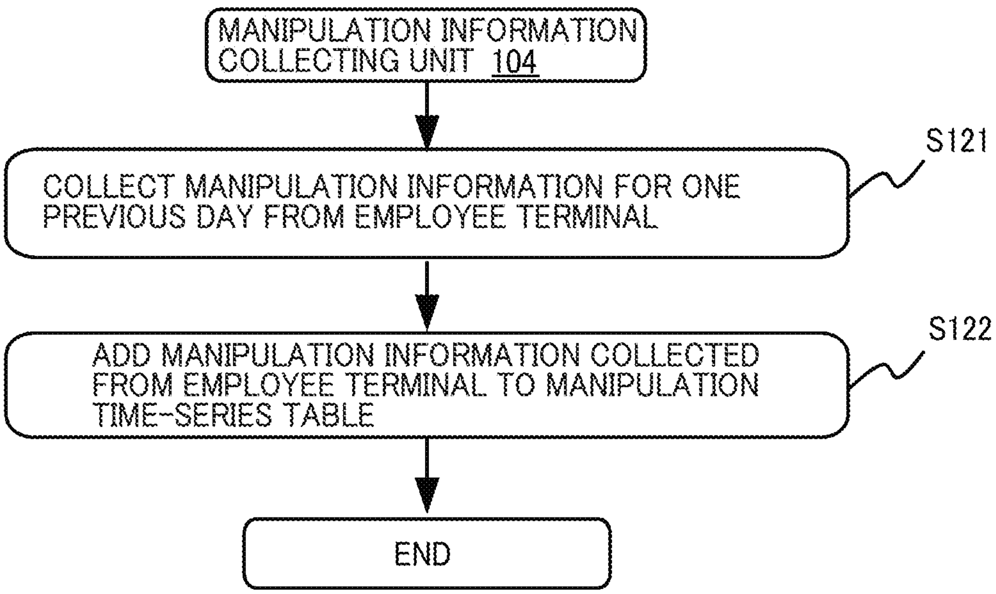
FIG. 5 is a diagram illustrating a second flow example of the mood score calculation method according to an embodiment of the invention.

FIG. 5 is a diagram illustrating a second flow example of the mood score calculation method according to this embodiment. Specifically, the FIG. 5 illustrates an operation flow example of the manipulation information collecting unit 104 of the administrator terminal 103.

In this case, the manipulation information collecting unit 104 of the administrator terminal 103 collects the manipulation information 140, for example, of one previous day from the employee terminals 101A to 101C.

In this case, the manipulation information collecting unit 104 instructs each of the employee terminals 101A to 101C to transmit the manipulation information by designating a period of time. Meanwhile, each of the manipulation information acquiring units 102A to 102C of the employee terminals 101A to 101C transmits the manipulation information 140 corresponding to the period to time instructed from the administrator terminal 103 to the administrator terminal 103.

Subsequently, the manipulation information collecting unit 104 of the administrator terminal 103 adds the manipulation information 140 collected from the employee terminals 101A to 101C described above to the manipulation time-series table 105 (S122) and terminates the process.

FIG. 6 illustrates an exemplary configuration of the manipulation time-series table 105 of the administrator terminal 103 according to this embodiment. The manipulation time-series table 105 according to this embodiment has a table structure similar to that of the manipulation information 140 described above.

Specifically, the manipulation time-series table 105 includes an employee terminal ID column 151, a date column 152, a time column 153, an event name column 154, a key type column 155, and an application name column 156.

Figure 7A:
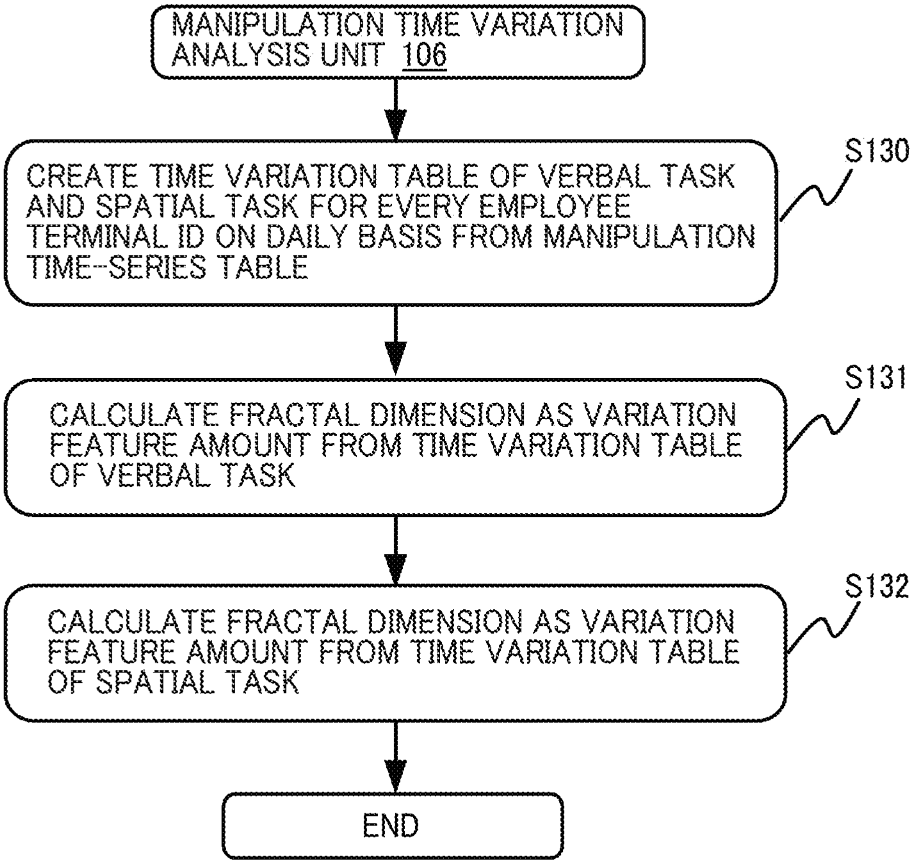
FIG. 7A is a diagram illustrating a third flow example of the mood score calculation method according to an embodiment of the invention.

FIG. 7A is a diagram illustrating a third flow example of the mood score calculation method according to this embodiment. Specifically, FIG. 7A illustrates an operation flow example of the manipulation time variation analysis unit 106 of the administrator terminal 103.

In this case, the manipulation time variation analysis unit 106 of the administrator terminal 103 creates time variation tables of each of the verbal task and the spatial task for every employee terminal ID on a daily basis from the manipulation time-series table 105 (S130).

In this case, it is assumed that the manipulation time variation analysis unit 106 selects a record of a predetermined target event set in advance, that is, a record of the manipulation information executed by an application corresponding to the verbal task or the spatial task as described above for every employee terminal ID on a daily basis from the manipulation time-series table 105 and creates the time variation table. A single time variation table represents event information regarding the verbal task or the spatial task of a single employee terminal for a single day.

FIG. 8 illustrates an exemplary configuration of the time variation table 160 created by the manipulation time variation analysis unit 106. FIG. 8 illustrates the time variation table 160 extracted from the manipulation time-series table 105 under a condition in which the employee terminal ID is set to "PC0001", the date is set to "2014/03/13", the application name is set to "table calculation" or "document creation" (that is, corresponding to the verbal task), and the event name is set to "KEY_DOWN".

The time variation table 160 of FIG. 8 has a record number (#) column 161 and a time column 162. The time column 162 shows occurrence timings of each target event. In this example, the target event is a keydown (key input).

In the example of FIG. 8, information on only a single type of event is extracted. Alternatively, the manipulation time variation analysis unit 106 may extract information on a plurality of types of events. A plurality of types of events may include events on the same input device or events on different input devices. A condition for extracting the events may include conditions other than the event name.

Subsequently, the manipulation time variation analysis unit 106 calculates a fractal dimension as a feature amount for a variation of the manipulation time interval in manipulations performed on each employee terminal 101A to 101C for a predetermined period of time from items of the time variation table created in step S130 described above regarding the verbal task (S131).

In this example, a fractal dimension of the manipulation time for a manipulation for a single day is calculated as the feature amount of the variation of the manipulation time interval in manipulations for a predetermined period of time. The manipulation time interval is a time interval between manipulations performed for the target. The predetermined period of time is determined depending on design.

As a method of calculating the fractal dimension "d", for example, a box counting method is known in the art. A sequence of calculating the fractal dimension "d" in this box counting method is set as follows as described in the flowchart of FIG. 7B. Note that the fractal dimension "d" based on the box counting method is defined as expressed in the following Formula 1.

$$d = -\lim_{\delta \to 0} \frac{\log N(\delta)}{\log \delta} \qquad (1)$$

Here, "δ" denotes a time segmentation window size, and "N" denotes the number of time segmentation windows having one or more target events.

The manipulation time variation analysis unit 106 calculates a total number K of the target events in the time variation table created regarding the verbal task as described above (S142). The total number K of the target events matches the number of records of the time variation table. In the aforementioned example, the total number K of target events is frequency of the keydown manipulation performed on the employee terminal 101 for a single day regarding the verbal task.

The manipulation time variation analysis unit 106 compares the total number K of the target events with a predetermined threshold value K_th (S143). If the total number K of the target events is equal to or greater than the threshold value K_th as a result of this comparison (S143: otherwise), the manipulation time variation analysis unit 106 calculates the number N[i] of time segmentation windows having one or more target events in each of different time segmentation window sizes δ[i] (where i=0, . . . , M−1, unit: second) (S144).

Figure 9:
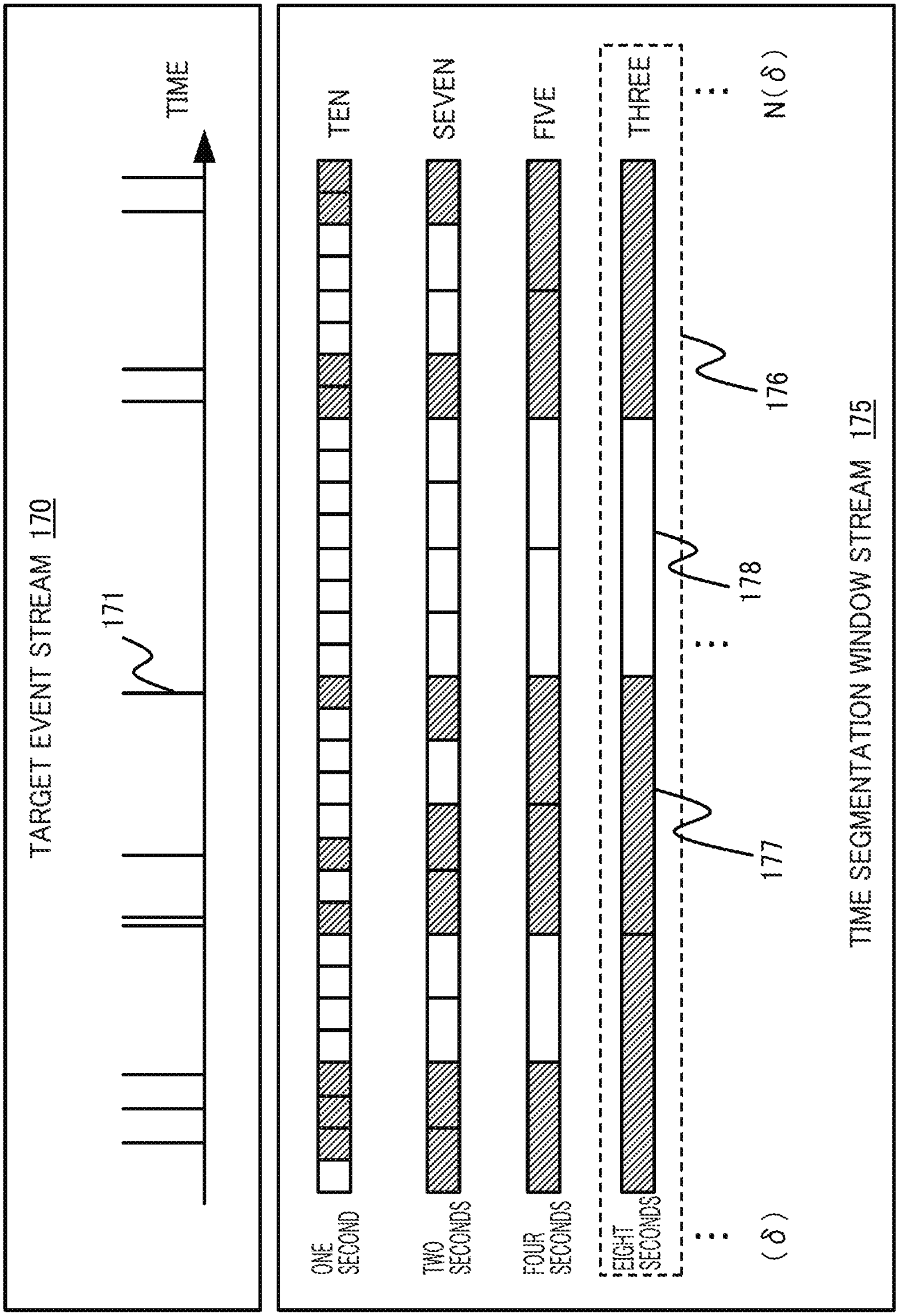
FIG. 9 is a diagram illustrating an exemplary concept of calculating the number N[i] of time segmentation windows according to an embodiment of the invention.

FIG. 9 illustrates an exemplary method of calculating the number N[i] of time segmentation windows. The section 170 represents a time series of the target events for a single day performed on a single employee terminal. A single line 171 on the time axis represents a single target event (keydown).

The section 175 represents a time segmentation window stream having different time segmentation window sizes δ[i] (where i=0, . . . , M−1). In this example, the time segmentation window size δ[i] is set to 2^I (where i=0, . . . , M−1), and "M" denotes an integer equal to or greater than "2".

In this case, the manipulation time variation analysis unit 106 calculates the number N[i] of the time segmentation window having one or more target events while changing the time segmentation window size δ[i]=2^i (where i=0, . . . , M−1, unit: second).

For example, in the time segmentation window stream 176 having a time segmentation window size of 8 seconds (δ[3]), the number N[3] of the time segmentation windows having one or more target events is "3". The hatched time segmentation windows (such as the time segmentation window 177) are time segmentation windows having one or more target events. The blanked time segmentation windows (such as the time segmentation window 178) are time segmentation windows having no target event. In addition, the numbers N of the time segmentation windows having one or more target events for the time segmentation window sizes of 1, 2, and 4 seconds are set to "10, "7", and "5", respectively.

Figure 7B:
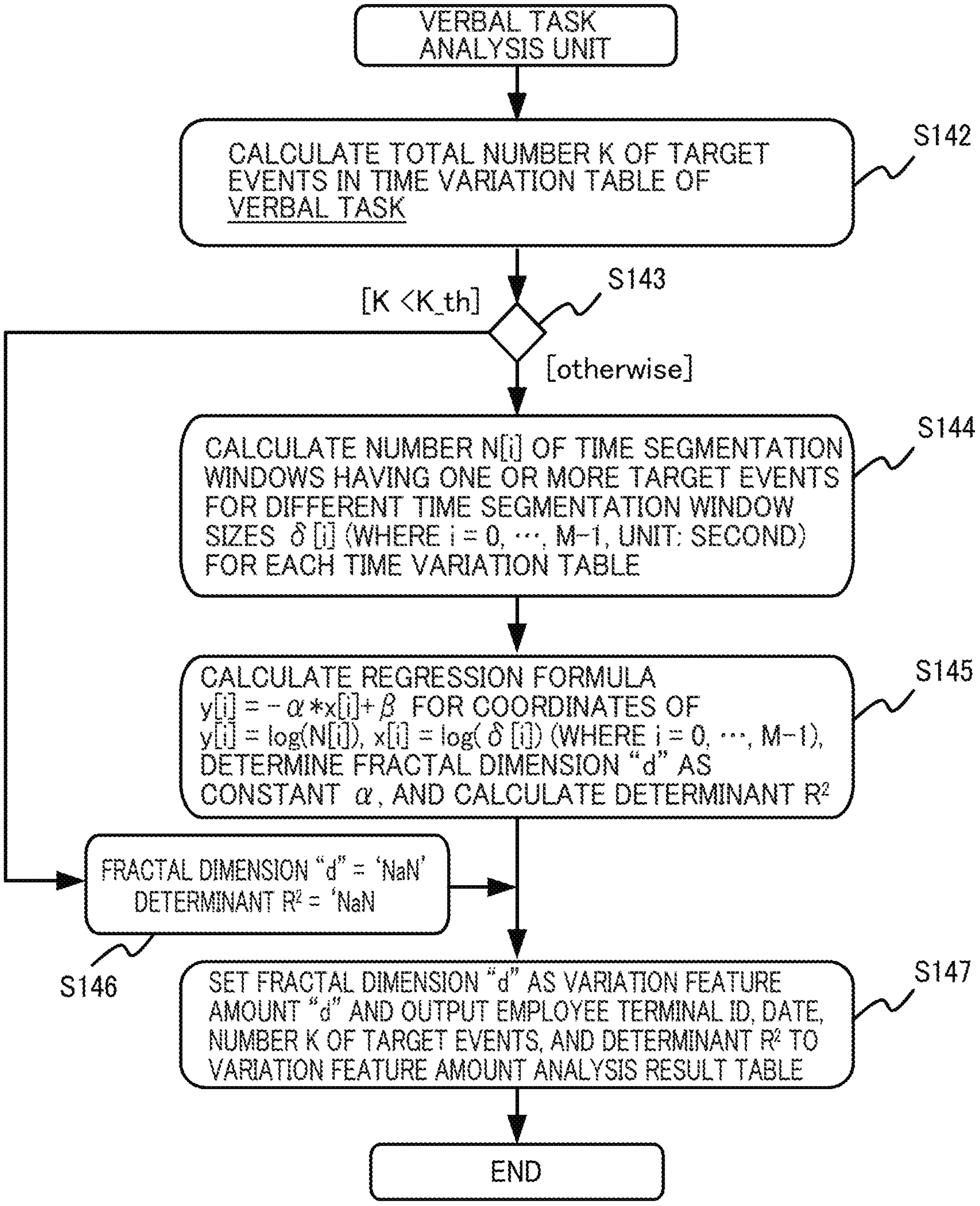
FIG. 7B is a diagram illustrating a fourth flow example of the mood score calculation method according to an embodiment of the invention.
Figure 7C:
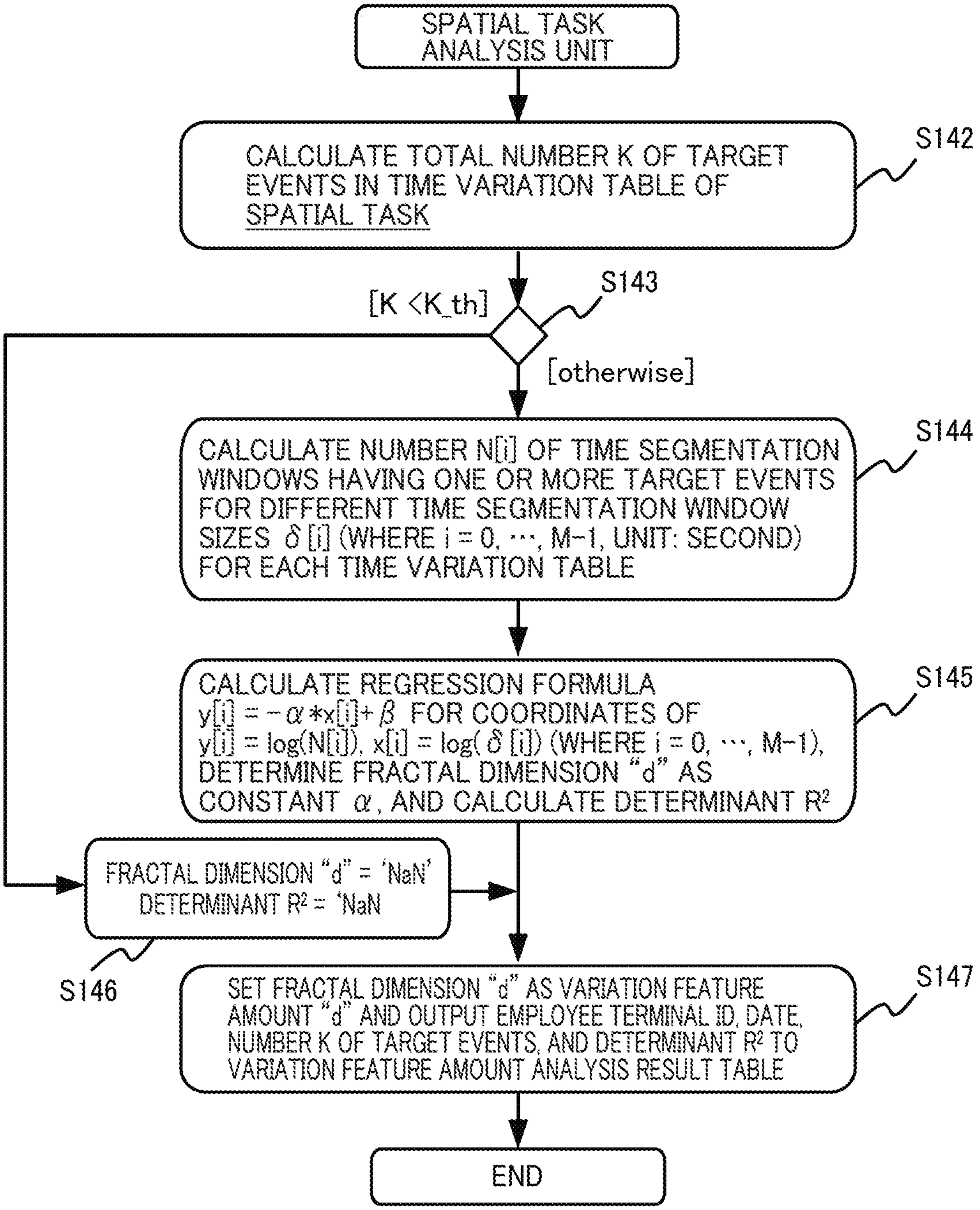
FIG. 7C is a diagram illustrating a fifth flow example of the mood score calculation method according to an embodiment of the invention.

Returning to the flowchart of FIG. 7B, the manipulation time variation analysis unit 106 calculates a double logarithmic chart (double logarithmic relationship) between the time segmentation window size δ[i] and the number N[i] and calculates a slope of an approximation straight line (S145). That is, the manipulation time variation analysis unit 106 calculates coordinates of "y[i]=log(N[i])" and "x[i]=log (δ[i])" (where i=0, . . . , M−1) and determines a regression formula "y[i]=−α*x[i]+β".

The manipulation time variation analysis unit 106 calculates the constants α and β on the basis of, for example, a least square method. The manipulation time variation analysis unit 106 determines the slope α as the fractal dimension "d". In addition, the manipulation time variation analysis unit 106 calculates a determinant $R^2$ indicating a matching degree of the coordinates to the regression formula.

Figure 10:
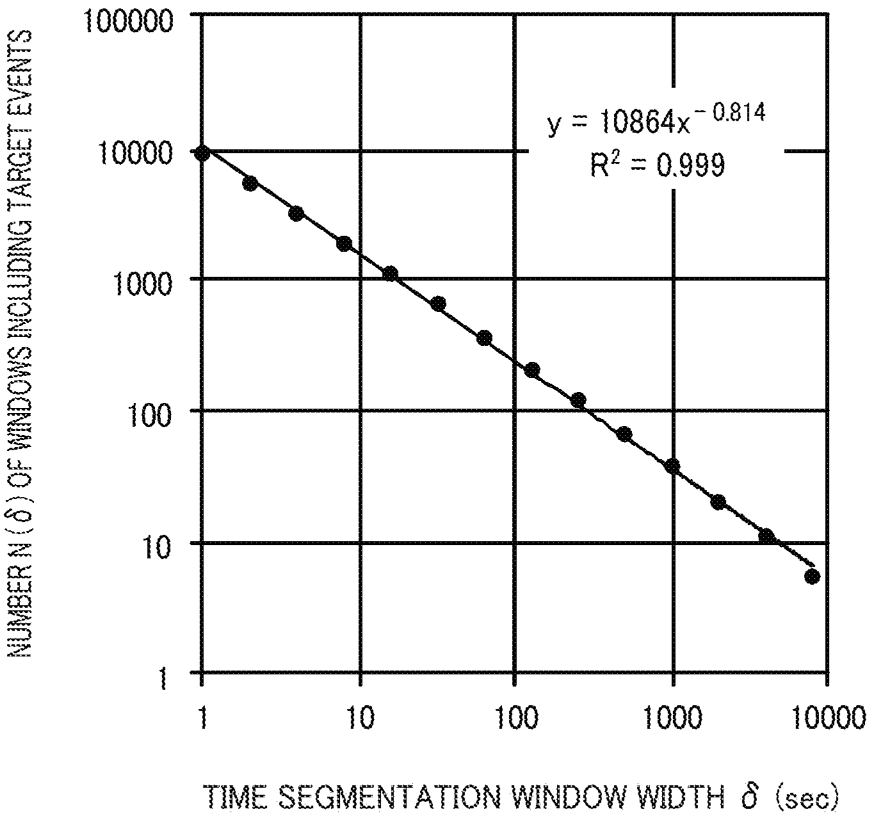
FIG. 10 is a diagram illustrating an exemplary double logarithmic chart and an exemplary regression line regarding a time segmentation window size δ[i] and the number N[i] of the time segmentation windows including target events according to an embodiment of the invention.

FIG. 10 illustrates an exemplary double logarithmic chart and an exemplary regression line regarding the time segmentation window size δ[i] and the number N[i] of the time segmentation windows having target events. Each point on FIG. 10 indicates a real measurement value, and the straight line indicates a regression line of the real measurement values. In addition, a slope −α of the regression line is set to "−0.814", and the fractal dimension "d" is set to "0.814". In addition, the determinant $R^2$ is set to "0.999".

As recognized from FIG. 10, a time interval of key depression indicates a fracture nature with high accuracy. The inventors measured the manipulation time interval many times. As a result of the measurement, it was found that the fracture nature is established with high accuracy.

Returning to the flowchart of FIG. 7B, if the total number K of target events is smaller than the threshold value K_th in step S143 described above (S143: K<K_th), the manipulation time variation analysis unit 106 determines the fractal dimension "d" as "NaN" and determines the determinant $R^2$ as "NaN" (S146).

The aforementioned value "NaN" is an error value indicating that the computation result is abnormal. If the total number K of target events is small, it is difficult to accurately calculate the fractal dimension and the mood score. Therefore, it is possible to avoid providing erroneous information on the employee's mood by presenting "not a number (NaN)".

Finally, the manipulation time variation analysis unit 106 outputs the fractal dimension "d" obtained regarding the verbal task along with the employee terminal ID, the date, the total number K of target events, and the determinant $R^2$ to the feature amount analysis result table as a variation feature amount "d" of the terminal manipulation time interval (S147) and terminates the process. The feature amount analysis result table is stored in the secondary memory 123.

FIG. 11 illustrates an exemplary configuration of the feature amount analysis result table 180. The feature amount analysis result table 180 includes an employee terminal ID column 181, a date column 182, a total number of target events column 183, a variation feature amount column 184, and a determinant column 185.

Note that the total number of target events column 183, the variation feature amount column 184, and the determinant column 185 are provided for both the verbal task and the spatial task. Therefore, information stored in the feature amount analysis result table 180 as result of the flowchart of FIG. 7B is stored in the columns of the verbal task.

A single record of the feature amount analysis result table 180 indicates information on a single employee terminal (a single employee) for a single day. As described above, the variation feature amount indicates the fractal dimension "d" of the manipulation time interval.

Although a box counting dimension is employed as the fractal dimension in the example described above, other types of fractal dimensions may also be employed. For example, the Lenny dimension, the Hausdorff dimension, the packing dimension, or the correlation dimension may be employed.

Here, returning to the flowchart of FIG. 7A, the manipulation time variation analysis unit 106 calculates the fractal dimension as a feature amount of the variation of the manipulation time interval in manipulations performed on each of the employee terminals 101A to 101C for a predetermined period of time from items regarding the spatial task of the time variation table created in step S130 as described above (S131). The process of calculating the fractal dimension regarding the spatial task is similar to the flow of calculating the fractal dimension regarding the verbal task described in conjunction with 7B except that the process starts by using the time variation table of the spatial task as a target. Therefore, it will not be described repeatedly. However, as a result of this flow, the records containing values corresponding to each column of the feature amount analysis result table 180 regarding the spatial task are stored.

That is, a data structure of each record of the feature amount analysis result table 180 is completed.

Figure 12:
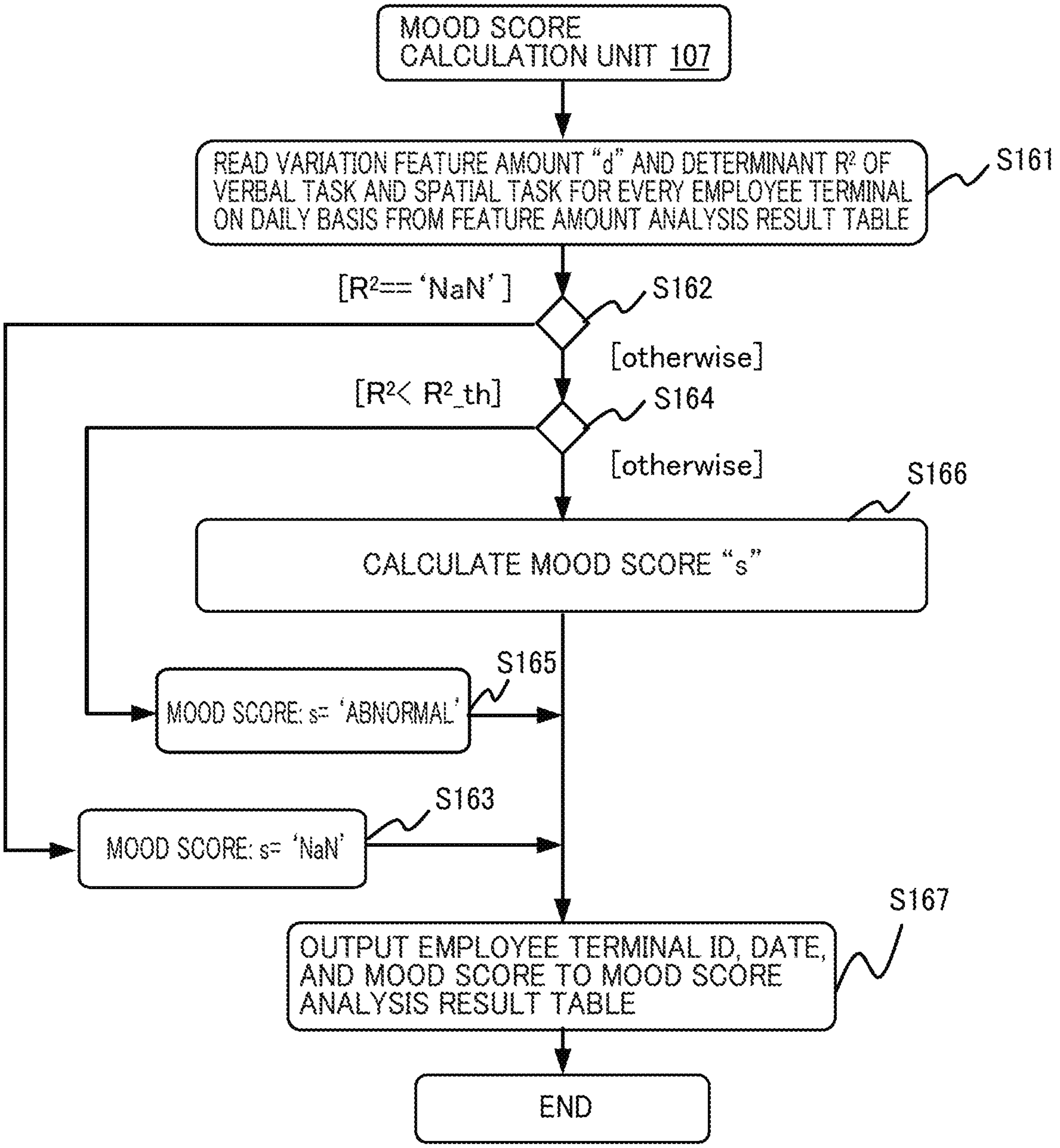
FIG. 12 is a diagram illustrating a sixth flow example of the mood score calculation method according to an embodiment of the invention.

Subsequently, a process of the mood score calculation unit 107 of the administrator terminal 103 will be described. FIG. 12 is a diagram illustrating a sixth flow example of the mood score calculation method according to this embodiment. Specifically, FIG. 12 illustrates an operation flow example of the mood score calculation unit 107. In this case, the mood score calculation unit 107 obtains the variation feature amounts regarding each of the verbal task and the spatial task from the feature amount analysis result table 180 created as described above and calculates the employee's mood score.

First, the mood score calculation unit 107 of the administrator terminal 103 reads the variation feature amount "d" and the determinant $R^2$ (record) of the verbal task and the spatial task for every employee terminal ID on a daily basis from the feature amount analysis result table 180 (S161). A single record represents information of a single employee terminal for a single day.

Subsequently, the mood score calculation unit 107 determines the mood score "s" of each employee terminal ID of each day. In the following description, a method of calculating the mood score of each record will be described.

The mood score calculation unit 107 determines whether or not the read determinant $R^2$ is set to "NaN" (S162). If the determinant $R^2$ is set to "NaN" (S162: R2=NaN), the mood score calculation unit 107 determines the mood score "s" of the corresponding record (the corresponding date of the corresponding employee terminal ID) as "NaN" (S163). It is possible to avoid providing erroneous information on the employee's mood by presenting error occurrence.

Otherwise, if the determinant $R^2$ is not set to "NaN" (S162: otherwise), the mood score calculation unit 107 compares the determinant $R^2$ with a predetermined threshold value $R^2$_th (S164).

If the determinant $R^2$ is smaller than the threshold value $R^2$_th as a result of this comparison (S164: $R^2$>$R^2$_th), the mood score calculation unit 107 determines that the mood score "s" of this record is "abnormal" (S165).

If the determinant $R^2$ is smaller, this means the manipulation time interval stream does not have the fractal nature. The inventors found that a typical manipulation time interval stream has the high fracture nature, and the fractal dimension is highly related with the mood score.

However, if the manipulation time interval stream does not have the high fractal nature, it is highly likely that the employee has a state different from a normal state. In this regard, if the determinant $R^2$ is smaller, a mental health manager is notified of abnormality so as to pay attention.

Otherwise, if the determinant $R^2$ is equal to or greater than the threshold value $R^2$_th as a result of the comparison described above (S164: otherwise), the mood score calculation unit 107 calculates the mood score "s" of this record on the basis of a predetermined formula (S166). Formula 2 is an exemplary formula for calculating the mood score "s".

$$s=a_1 d_V+a_2 d_S+a_3 \quad (2)$$

Here, $a_1$, $a_2$, and $a_3$ denote predetermined constant coefficients. Formula 2 provides relational information representing a relationship between the feature amount d_V of the verbal task (Verbal), the feature amount d_S of the spatial task (Spatial), and the mood score.

Formula 2 is used to calculate a mood score for one type of mood such as anger or anxiety. When a plurality of types of mood scores are calculated, a plurality of sets of coefficients $a_1$, $a_2$, and $a_3$ are Given in advance. The mood score calculation unit 107 calculates different types of mood scores, respectively, on the basis of Formula 2 using a set of coefficients $a_1$, $a_2$, and $a_3$.

Note that the coefficients $a_1$, $a_2$, and $a_3$ are determined in advance through experiments performed for the examinee. For example, a system designer may determine the coefficients $a_1$, $a_2$, and $a_3$ by comparing the fractal dimension calculated from the examinee's manipulation history with the examinee's mood score determined on the basis of the profile of mood state (POMS) technique, the Beck depression inventory Second edition (BDI-II), or the like. The coefficients $a_1$, $a_2$, and $a_3$ may be prepared commonly for all employees or individually for each employee.

Subsequently, the mood score calculation unit 107 outputs the employee terminal ID, the date, and the calculated mood score to the mood score analysis result table (S167).

FIG. 13 illustrates an exemplary configuration of the mood score analysis result table 190. The mood score analysis result table 190 has an employee terminal ID column 191, a date column 192, and a calculated mood score column 193. In this example, one type of the mood score is calculated for manipulations performed on a single employee terminal for a single day.

Figure 14:
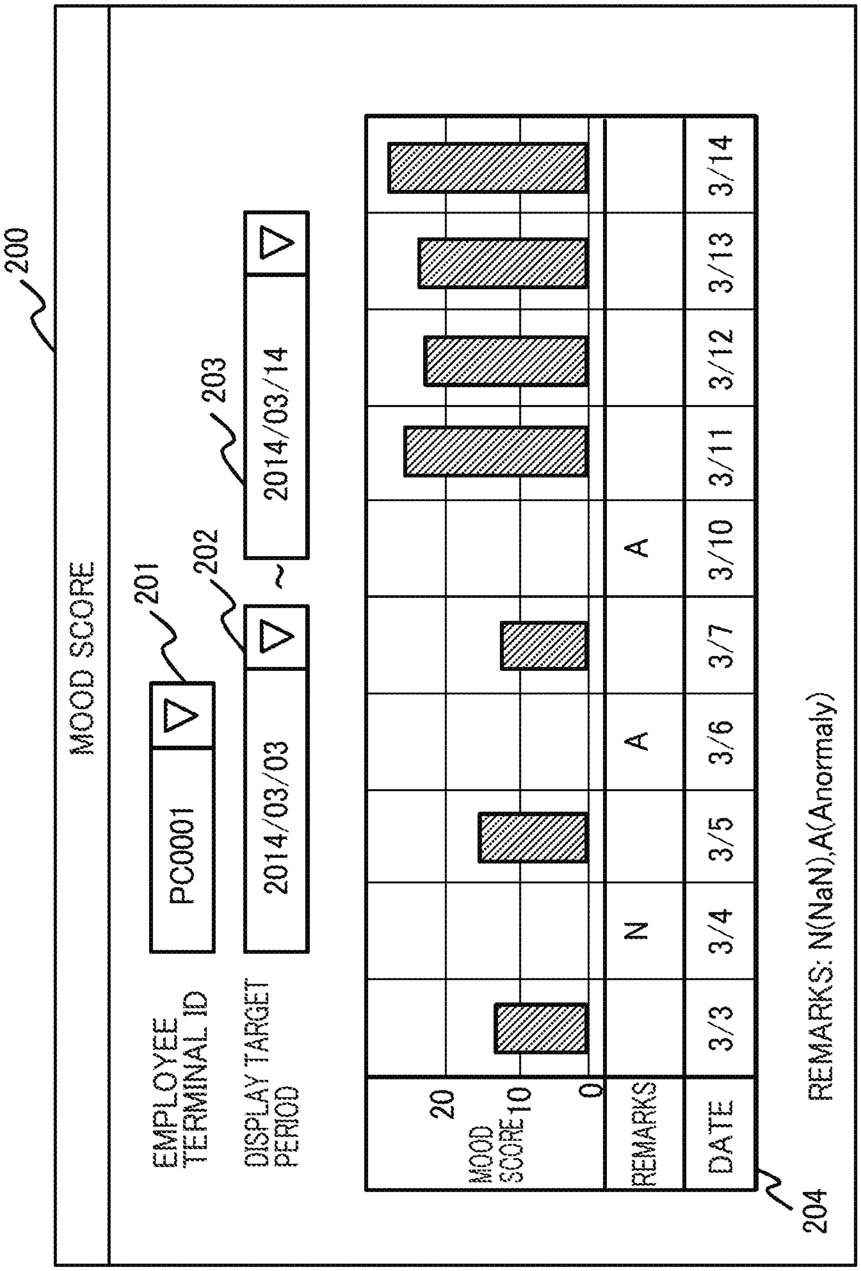
FIG. 14 is a diagram illustrating an exemplary mood score analysis result image according to an embodiment of the invention.

FIG. 14 illustrates an exemplary mood score analysis result image 200. A result display unit 108 of the administrator terminal 103 creates data on the mood score analysis result image from the mood score analysis result table 190 and displays the mood score analysis result image 200 on the display device 126.

The mood score analysis result image 200 of FIG. 14 includes a field 201 for selecting the employee terminal ID, fields 202 and 203 for inputting start and end of a display target period, and a section 204 for calculating the mood score.

The mental health manager selects an employee terminal ID for which the information on the mood score is displayed in the field 201 using the input device 125 of the administrator terminal 103 and inputs a period for displaying the information on the mood score into the fields 202 and 203.

Meanwhile, the result display unit 108 selects the mood score analysis result table 190 depending on the user's input described above and selects data requested by the user from the selected mood score analysis result table 190. In addition, the result display unit 108 creates image data on the section 204 for displaying the mood score and outputs the data to the display device 126.

The aforementioned section 204 contains the mood score of the selected employee terminal of each day for the selected period of time. The mood score is a value calculated by the corresponding user from the manipulation information for the corresponding period. This section 204 may contains information on the variation feature amount or information on the determinant in addition to the mood score.

Figure 15:
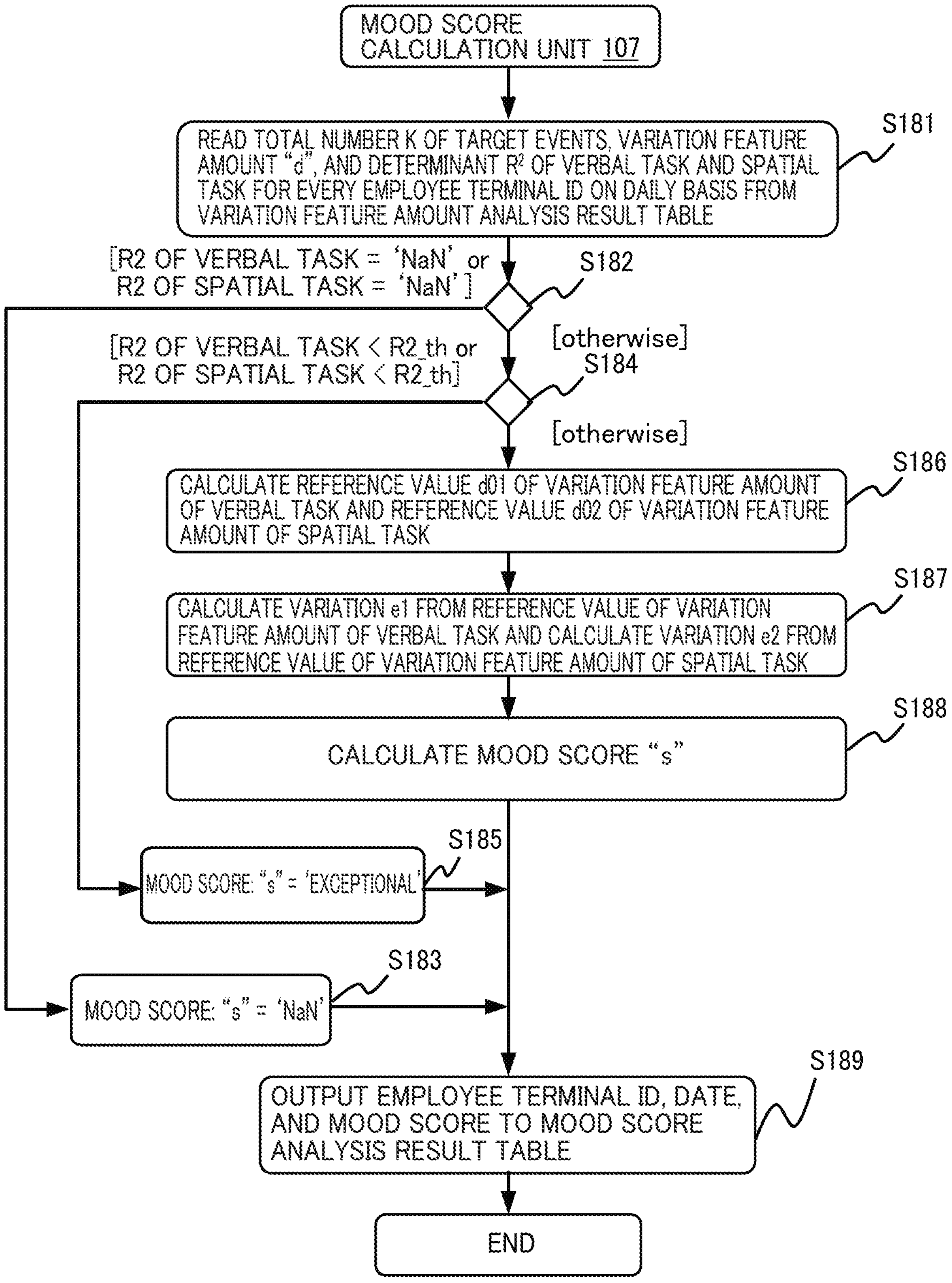
FIG. 15 is a diagram illustrating a seventh flow example of the mood score calculation method according to an embodiment of the invention.

FIG. 15 illustrates another example of the method of calculating the mood score using the mood score calculation unit 107. In this example, the mood score calculation unit 107 calculates a reference value of the feature amount of the variation using the total number K of target events and calculates the mood score on the basis of this reference value and the feature amount of the variation calculated by the manipulation time variation analysis unit 106. The following description will be made by focusing on a difference from the mood score calculation operation of FIG. 12.

The inventors found that the fractal dimension tends to increase as the total number K of target events increases. That is, when the employee is busy, the fractal dimension tends to increase regardless of the employee's mood. In this regard, in this example, the mood score calculation unit 107 calculates the fractal dimension and the mood score matching the employee's mood by subtracting a component caused by busyness from the value of the fractal dimension.

The mood score calculation unit 107 reads the variation feature amount "d", the total number K of target events, and the determinant $R^2$ (record) of each of the verbal task and the spatial task for every employee terminal ID on a daily basis from the feature amount analysis result table 180 (S181).

The mood score calculation unit 107 determines whether or not "NaN" is set in the read determinant $R^2$ for each of the verbal task and the spatial task (S182).

If any determinant $R^2$ is set to "NaN" as a result of the aforementioned determination (S182: $R^2$=NaN), the mood score calculation unit 107 determines that the mood score "s" of the corresponding record (the corresponding date of the corresponding employee terminal ID) is set to "NaN" (S183). It is possible to avoid providing erroneous information on the employee's mood by presenting error occurrence.

Otherwise, if the determinant $R^2$ is not set to "NaN" (S182: otherwise), the mood score calculation unit 107 compares the determinants $R^2$ of each of the verbal task and the spatial task with the predetermined threshold value $R^2$_th (S184).

If any determinant $R^2$ is smaller than the threshold value $R^2$_th as a result of the comparison (S164: $R^2$<$R^2$_th), the mood score calculation unit 107 determines the mood score "s" of the corresponding record as "exceptional" (S185).

In step S186, the mood score calculation unit 107 calculates the reference value d_V0 of the variation feature amount for the verbal task on the basis of a predetermined formula using the total number K_V of target events of the verbal task. An exemplary formula for calculating the reference value d_V0 of the variation feature amount of the verbal task is expressed in Formula 3a.

The mood score calculation unit 107 calculates a reference value d_S0 of the variation feature amount of the spatial task on the basis of a predetermined formula using the total number K_S of target events of the spatial task. An exemplary formula for calculating the reference value d_S0 of the variation feature amount of the spatial task is expressed in Formula 3b.

$$d_{V0}=b_{V1}+b_{V2}\log K_V \quad (3a)$$

$$d_{S0}=b_{S1}+b_{S2}\log K_S \quad (3b)$$

Here, b_V1, b_V2, b_S1, and b_S2 are constant coefficients given in advance. The constant coefficients b_V1, b_V2, b_S1, and b_S2 may be determined through experiments for the examinee. Formula 3a expresses information representing a relationship between the total number K_V of target events of the verbal task and the reference value d_V0. In addition, Formula 3b is information representing a relationship between the total number K_S of target events of the spatial task and the reference value d_S0.

Then, the mood score calculation unit 107 calculates the variation e_V from the reference value d_V0 of the variation feature amount d_V of the verbal task (S187). An exemplary formula for calculating the variation e_V is expressed in Formula 4a.

The mood score calculation unit 107 calculates the variation e_S from the reference value d_S0 of the variation feature amount d_S of the spatial task (S187). An exemplary formula for calculating the variation e_S is expressed in Formula 4b.

$$e_V=\frac{d_V}{d_{V0}}-1 \quad (4a)$$

$$e_S=\frac{d_S}{d_{S0}}-1 \quad (4b)$$

Next, the mood score calculation unit 107 calculates the mood score "s" on the basis of the variation e_V from the reference value d_V0 of the variation feature amount d_V of the verbal task and the variation e_S from the reference value d_S0 of the variation feature amount d_S of the spatial task (S188). An exemplary formula for calculating the mood score "s" is expressed in Formula 5.

$$s=c_1e_V+c_2e_S+c_3 \quad (5)$$

Here, $c_1$, $c_2$, and $c_3$ are constant coefficients given in advance. The constant coefficients $c_1$, $c_2$, and $c_3$ may be determined through experiments for the examinee.

Formula 5 expresses information representing a relationship between the variation and the mood score. Formulas 3a, 3b, 4a, 4b, and 5 represent a relationship among the variation feature amount d_V of the verbal task, the variation feature amount d_S of the spatial task, and the mood score "s". Formula 5 is used to calculate the mood score for a single type of mood. When a plurality of types of mood scores are calculated, a plurality of sets of coefficients $c_1$, $c_2$, and $c_3$ are provided in advance.

Finally, the mood score calculation unit 107 outputs the employee terminal ID, the date, and the calculated mood score to the mood score analysis result table (S189).

Figure 16A:
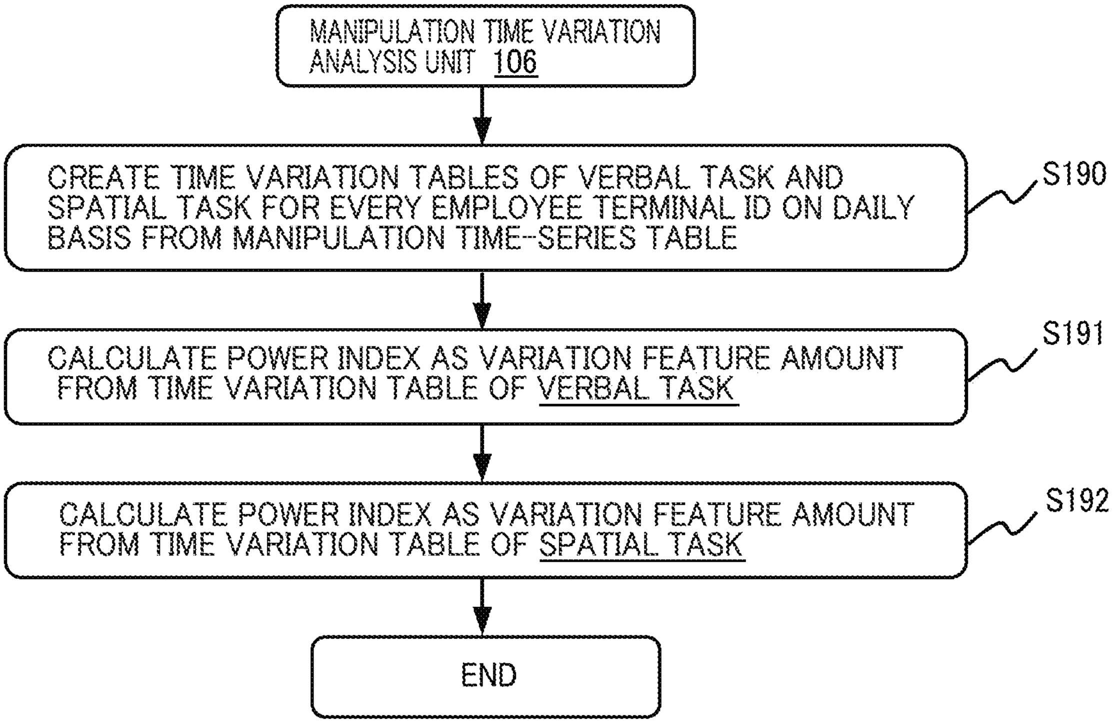
FIG. 16A is a diagram illustrating an eighth flow example of the mood score calculation method according to a method of an embodiment of the invention.

Here, another exemplary method of calculating the variation feature amount using the manipulation time variation analysis unit 106 will be described. FIG. 16A is a diagram illustrating an eighth flow example of the mood score calculation method according to this embodiment. Specifically, FIG. 16A illustrates another exemplary method of calculating the variation feature amount using the manipulation time variation analysis unit 106.

Note that, in this example, the manipulation time variation analysis unit 106 calculates the power index α by assuming a power distribution of the cumulative probability distribution of the time interval of the manipulation as the variation feature amount is set to "P(x>Δt)∝(Δt)−α". As a result, it is possible to more suitably calculate the mood score.

First, the manipulation time variation analysis unit 106 creates the time variation table for each of the verbal task and the spatial task for every employee terminal ID on a daily basis from the manipulation time-series table 105 (S190). Here, the timing of each record of the time variation table is defined as t[i] (where i=0, . . . , K−1).

Figure 17:
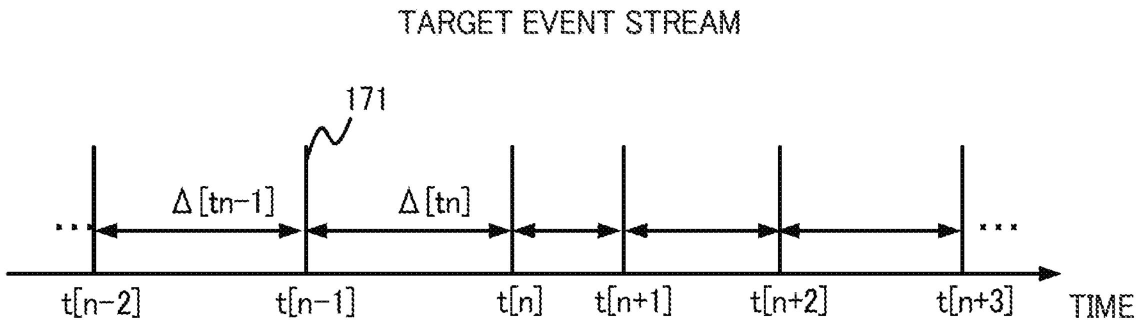
FIG. 17 is a diagram illustrating a time series of the daily target events of a single employee terminal according to an embodiment of the invention.

FIG. 17 illustrates a time series of target events of a single employee terminal for a single day. A single line 171 on the time axis indicates a single target event (key down). An occurrence timing of each event is denoted by "t[i]". A time interval between an event at the occurrence timing t[n−1] and an event at the occurrence timing t[n] is denoted by "Δt[n]".

Returning to the flow of FIG. 16A, subsequently, the manipulation time variation analysis unit 106 calculates a power index as a variation feature from the time variation table 160 obtained for the verbal task (S191).

Figure 16B:
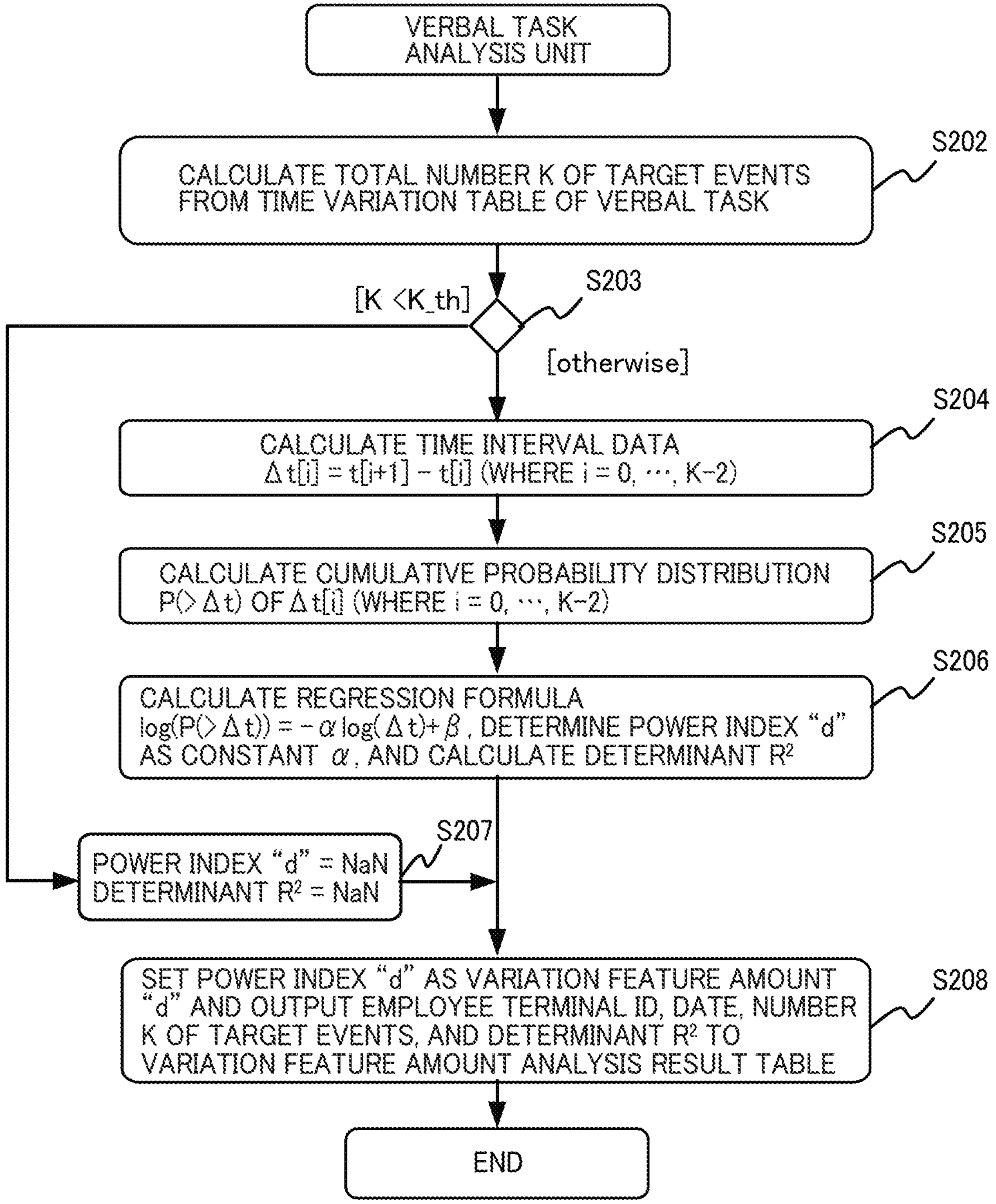
FIG. 16B is a diagram illustrating a ninth flow example of the mood score calculation method according to a method of an embodiment of the invention.

In this case, as illustrated in the flow of FIG. 16B, the manipulation time variation analysis unit 106 calculates the total number K of target events from the time variation table 160 regarding the verbal task (S202). The total number K of target events of the time variation table 160 is the number of records in the time variation table 160.

In the following description, the manipulation time variation analysis unit 160 executes steps S203 to S207 for the time variation table regarding the verbal task. Here, the manipulation time variation analysis unit 106 compares the total number K of target events with the threshold value K_th for this time variation table 160 (S203).

If the total number K of target events is equal to or greater than the threshold value K_th as a result of the comparison described above (S203: otherwise), the manipulation time variation analysis unit 106 calculates time interval data "$\Delta t[i]=t[i+1]-t[i]$ (where i=0, . . . , K−2)" (S204). The time interval data $\Delta t$ [i] represents a time interval between successive events.

Then, the manipulation time variation analysis unit 106 calculates the cumulative probability distribution $P(>\Delta t)$ of the time interval data "$\Delta t[i]$ (where i=0, . . . , K−2)" (S205).

The manipulation time variation analysis unit 106 calculates a double logarithmic chart (double logarithmic relationship) between the time interval $\Delta t$ and the cumulative probability distribution $P(>\Delta t)$ and calculates a slope of an approximation straight line (S206).

That is, the manipulation time variation analysis unit 106 calculates coordinates "$y[i]=P(>\Delta t[i])$" and "$x[i]=\Delta t[i]$" (where i=0, . . . , K−2) and determines a regression formula "$\log(y)=-\alpha \log(x)+\beta$".

The manipulation time variation analysis unit 106 calculates constants $\alpha$ and $\beta$, for example, on the basis of the least square method. The manipulation time variation analysis unit 106 determines the slope a as the power index "d". In addition, the manipulation time variation analysis unit 106 calculates the determinant $R^2$ indicating a matching degree of the coordinates to the regression formula.

Figure 18:
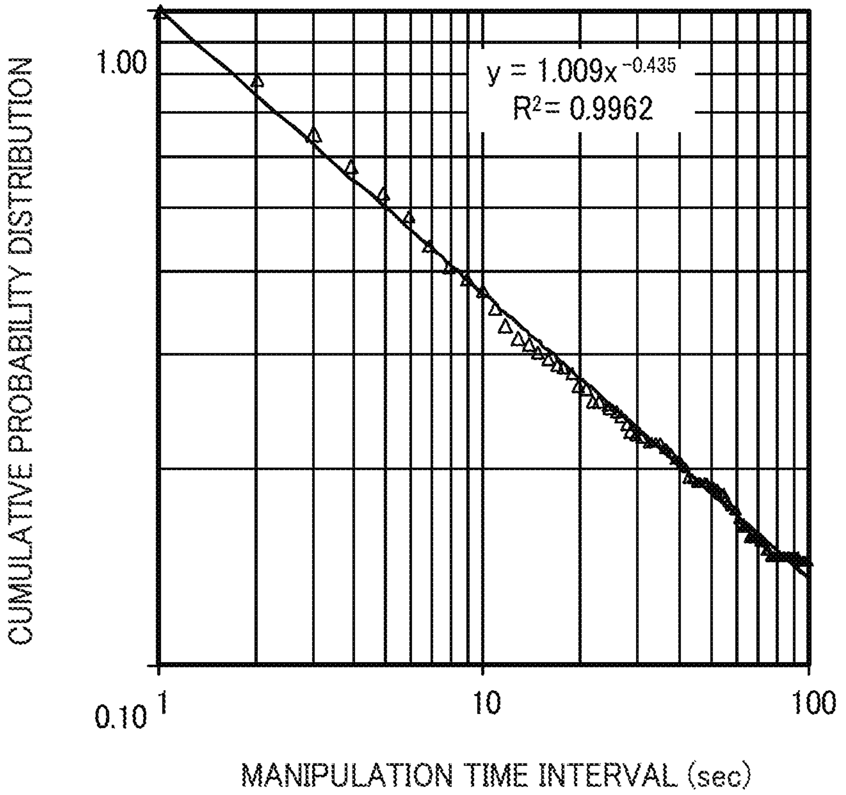
FIG. 18 is a diagram illustrating an exemplary double logarithmic chart and an exemplary regression line for a time interval Δt and a cumulative probability distribution P(x>Δt) according to an embodiment of the invention.

FIG. 18 illustrates an exemplary double logarithmic chart and an exemplary regression line for the time interval $\Delta t$ and the cumulative probability distribution $P(>\Delta t)$. FIG. 18 indicates the real measurement value. The slope "$-\alpha$" of the regression line is set to "−0.435" and the power index "d" is set to "0.435". In addition, the determinant $R^2$ is set to "0.9962".

As recognized from FIG. 18, a time interval for the key input is based on the power law with high accuracy. The inventors measured the manipulation time interval many times, and found that, as a result of the measurement, the power law is established with high accuracy.

Here, returning to FIG. 16B, if the total number K of target events is smaller than the threshold value K_th in step S203 described above (S203: K<K_th), the manipulation time variation analysis unit 106 determines the power index "d" as "NaN" and determines the determinant $R^2$ as "NaN" (S207).

Finally, the manipulation time variation analysis unit 106 outputs the power index "d" along with the employee terminal ID, the date, the total number K of target events, and the determinant $R^2$ as the variation feature amount "d" of the terminal manipulation time interval for the verbal task to the feature amount analysis result table 180 (S208).

Here, returning to the flow of FIG. 16A, after step S191, the manipulation time variation analysis unit 106 calculates the power index as a variation feature from the time variation table 160 obtained for the spatial task (S192), and terminates the process.

The process of calculating the power index for the spatial task is similar to the flow of calculating the power index for the verbal task in FIG. 16B except that the process starts by setting the time variation table for the spatial task as a target, and it will not be described repeatedly. However, as a result of this flow, records in which corresponding values are set in each column of the spatial task are stored in the feature amount analysis result table 180. That is, a data structure of each record of the feature amount analysis result table 180 is completed.

Figure 16C:
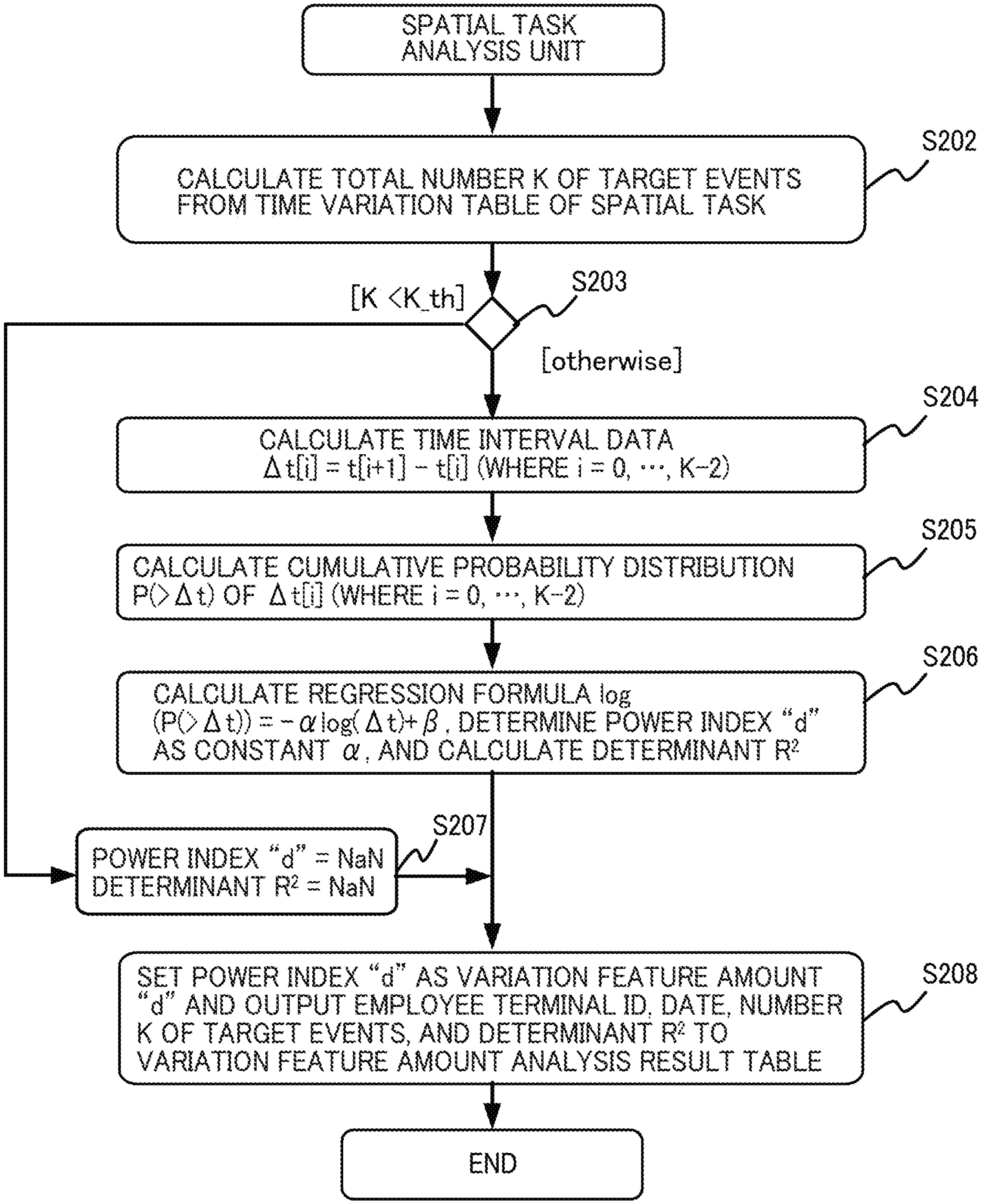
FIG. 16C is a diagram illustrating a tenth flow example of the mood score calculation method according to a method of an embodiment of the invention.

Using the variation feature amount "d" for each of the verbal task and the spatial task calculated with reference to each flowchart of FIGS. 16B and 16C, the mood score can be calculated on the basis of the method described in conjunction with FIG. 12 or 15.

Note that various modifications may be possible without limiting to the aforementioned examples. For example, while the examples have been described in details in order to facilitate understanding of the invention, it is not necessary to have all of the elements described above. In addition, a part of the configuration of a certain example may be substituted with those of other examples, and any one of configurations of other examples may be added to any example. Furthermore, any addition, deletion, or substitution may be possible for any part of the configurations of each example.

Each configuration, function and processing unit described above may be partly or entirely implemented by designing hardware such as an integrated circuit. Each of the configurations and functions described above may also be implemented as software by causing a processor to analyze and execute programs for implementing each function. Information such as programs, tables, or files for implementing each function may be stored in a memory, a recording device such as a hard disk drive (HDD) or a solid state device (SSD), or a recording medium such as an integrated circuit (IC) card or a secure digital (SD) memory card.

Control lines or information lines indicate what is considered to be necessary for explanation, and it is difficult to say that all of them are illustrated on the product. In fact, the readers may think that almost all the configurations are coupled to each other.

According to the embodiments of the invention, it is possible to easily and accurately specify a worker's mental health state in a form less burdensome for the worker.

The readers may recognize the following fact by reading this specification. Specifically, in the mood score calculation apparatus according to the embodiment of the invention, the arithmetic device may classify the manipulation history into anyone of the verbal task and the spatial task on the basis of the type of the apparatus used by the user indicated by the manipulation history when the manipulation history is classified.

As a result, it is possible to efficiently and accurately perform classification of the manipulation history, for example, by defining, in advance, that a keyboard for inputting or editing text is a device used for the verbal task, and a mouse for processing and editing graphics or images is a device used for the spatial task. Furthermore, it is possible to more easily and accurately specify the worker's mental health state in a form less burdensome for the worker.

In the mood score calculation apparatus according to the embodiment of the invention, the arithmetic device may classify the manipulation history into any one of the verbal task and the spatial task on the basis of the type of the application used by the user indicated by the manipulation history when the manipulation history is classified.

As a result, it is possible to efficiently and accurately perform classification of the manipulation history, for example, by defining, in advance, that a text editor for inputting or editing text is an application used for the verbal task, and an image editor for processing and editing graphics or images is an application used for the spatial task. Furthermore, it is possible to more easily and accurately specify the worker's mental health state in a form less burdensome for the worker.

In the mood score calculation apparatus according to the embodiment of the invention, the memory device may store a manipulation history for a routine manipulation performed by a user one or more times for a predetermined period of time as a user's manipulation history on a predetermined device. In addition, the arithmetic device may classify the manipulation history for the routine manipulation into any one of the verbal task or the spatial task on the basis of a predetermined algorithm, calculate a mood score of the user on the basis of a relative relationship between the manipulation histories of the routine manipulations for the verbal task and the spatial task specified by the aforementioned classification, and output the information on the mood score to a predetermined output target.

As a result, for example, it is possible to classify a simple manipulation performed by a user unconsciously with the same content at every predetermined opportunity such as PC start-up and screen lock cancellation, that is, the manipulation history for the routine manipulation, into any one of the verbal task and the spatial task and use the result in the mood score calculation. Furthermore, it is possible to more easily and accurately specify the worker's mental health state in a form less burdensome for the worker.

In the mood score calculation method according to the embodiment of the invention, the information processing device may classify the manipulation history into any one of the verbal task and the spatial task on the basis of the type of the device used by the user indicated by the manipulation history when the manipulation history is classified.

In the mood score calculation method according to the embodiment of the invention, the information processing device may classify the manipulation history into any one of the verbal task or the spatial task on the basis of the type of the application used by the user indicated by the manipulation history when the manipulation history is classified.

In the mood score calculation method according to the embodiment of the invention, the information processing device may allow the memory device to store a manipulation history for a routine manipulation performed by a user one or more times for a predetermined period of time as a user's manipulation history on a predetermined device, classify the manipulation history for the routine manipulation into any one of the verbal task or the spatial task on the basis of a predetermined algorithm, calculate a mood score of the user on the basis of a relative relationship between the manipulation histories of the routine manipulations for the verbal task and the spatial task specified by the aforementioned classification, and output the information on the mood score to a predetermined output target.

What is claimed is:

1. A mood score calculation apparatus for specifying an employee's mental health state without imposing a burden on the employee, the mood score calculation apparatus comprising:

an administrator terminal including a manipulation information collection unit, a manipulation time variation analysis unit, a mood score calculation unit, and a result display unit;

at least one employee terminal, the employee terminal including at least a keyboard for generating key inputs obtained by the employee while carrying out tasks during the course of employment, the at least one employee terminal having a manipulation information acquiring unit for acquiring a manipulation history of the employee including the key inputs obtained from the employee, the manipulation information acquiring unit including a memory device that stores the manipulation history of the employee on the at least one employee terminal;

a network provided for transmitting the manipulation histories from the at least one employee terminal to the manipulation information collection unit; and, an arithmetic device that classifies the manipulation history into any one of a verbal task and a spatial task on the basis of the type of input device or application used by the employee as indicated by the manipulation history, and utilizes the manipulation time variance analysis unit to determine a variation of the manipulation time interval in each manipulation of a verbal task and a spatial task of each employee by creating a table setting forth variations in manipulation time intervals for verbal tasks and variations in manipulation time intervals for spatial tasks for each employee and calculating a fractal dimension based upon said variations within a predetermined period of time, the manipulation time variance analysis unit determining a regression formula having coordinates and calculating a determinant indicating a matching degree of the coordinates of the regression formula to calculate a mood score of the employee, wherein if the determinant is smaller than a threshold value represented by the fractal dimension, then the mood score is determined to be abnormal, and outputs information on the mood score to generate a mood score analysis result image arranged to be displayed by the result display unit on a display device, the mood score analysis result image including a field for selecting an employee terminal ID, fields for inputting start and end of a display target period, and a section for calculating the mood score.

2. The mood score calculation apparatus according to claim 1, wherein the memory device stores a manipulation history for a routine manipulation performed by an employee one or more times for a predetermined period of time as an employee's manipulation history on a predetermined device, and the arithmetic device classifies the manipulation history of the routine manipulation into any one of the verbal task and the spatial task on the basis of a predetermined algorithm, calculates the mood score of the employee on the basis of a relative relationship between the manipulation histories of the routine manipulations for each of the verbal task and the spatial task specified in the classification, and outputs information on the mood score to a predetermined output target.

3. A mood score calculation method for specifying an employee's mental health state without imposing a burden on the employee, the method implemented by an information processing device, the method comprising:

providing an administrator terminal including a manipulation information collection unit, a manipulation time variation analysis unit, a mood score calculation unit, and a result display unit;

providing at least one employee terminal including at least a keyboard for generating key inputs obtained by an employee while carrying out tasks during the course of employment, the at least one employee terminal having a manipulation information acquiring unit for acquiring a manipulation history of the employee including the key inputs obtained from the employee, the manipulation information acquiring unit including a memory device that stores the manipulation history of the employee on the at least one employee terminal providing a network for transmitting the manipulation histories from the at least one employee terminal to the manipulation information collection unit;

classifying the manipulation history into any one of a verbal task and a spatial task on the basis of the type of input device or application used by the employee as indicated by the manipulation history;

utilizing the manipulation time variance analysis unit to determine a variation of the manipulation time interval in each manipulation of a verbal task and a spatial task of each employee by creating a table setting forth variations in manipulation time intervals for verbal tasks and variations in manipulation time intervals for spatial tasks for each employee and calculating a fractal dimension based upon said variations within a predetermined period of time, and utilizing the manipulation time variance analysis unit to determine a regression formula having coordinates and to calculate a determinant indicating a matching degree of the coordinates of the regression formula to calculate a mood score of the employee wherein if the determinant is smaller than a threshold value represented by the fractal dimension, then the mood score is determined to be abnormal; and, outputting information on the mood score to generate a mood score analysis result image arranged to be displayed by the result display unit on a display device, the mood score analysis result image including a field for selecting an employee terminal ID, fields for inputting start and end of a display target period, and a section for calculating a mode score.

4. The mood score calculation method according to claim 3, wherein the information processing device causes the memory device to store a manipulation history for a routine manipulation performed by an employee one or more times for a predetermined period of time as an employee's manipulation history on a predetermined device, and the information processing device classifies the manipulation history of the routine manipulation into any one of the verbal task and the spatial task on the basis of a predetermined algorithm, calculates the mood score of the employee on the basis of a relative relationship between the manipulation histories of the routine manipulations for each of the verbal task and the spatial task specified in the classification, and outputs information on the mood score to a predetermined output target.

* * * * *